United States Patent [19]

Fujiwhara et al.

[11] 4,200,466
[45] Apr. 29, 1980

[54] LIGHT-SENSITIVE SILVER HALIDE PHOTOGRAPHIC MATERIALS

[75] Inventors: Mitsuto Fujiwhara; Syunji Matsuo; Mikio Kawasaki; Toyoaki Masukawa; Yutaka Kaneko, all of Hino, Japan

[73] Assignee: Konishiroku Photo Industry Co., Ltd., Tokyo, Japan

[21] Appl. No.: 874,056

[22] Filed: Feb. 1, 1978

Related U.S. Application Data

[63] Continuation-in-part of Ser. No. 726,635, Sep. 27, 1976, abandoned.

[30] Foreign Application Priority Data

Sep. 30, 1975 [JP] Japan ................... 50-118480

[51] Int. Cl.$^2$ ................................................ G03C 1/06
[52] U.S. Cl. .................... 430/566; 430/543; 430/552

[58] Field of Search ................... 96/100 R, 55, 66 R, 96/82, 95

[56] References Cited

U.S. PATENT DOCUMENTS

| | | | |
|---|---|---|---|
| 2,181,944 | 12/1939 | Kleine et al. | 96/100 R |
| 2,728,660 | 12/1955 | Salminen et al. | 96/100 R |
| 3,222,176 | 12/1965 | Jaeken | 96/100 R |
| 3,516,831 | 6/1970 | Wolf et al. | 96/100 R |
| 3,622,629 | 11/1971 | Lugosy | 96/66 R |
| 3,674,490 | 7/1972 | Matejec | 96/77 |
| 3,820,991 | 6/1974 | Van Doorselaer et al. | 96/82 |

*Primary Examiner*—Travis Brown
*Attorney, Agent, or Firm*—Bierman & Bierman

[57] ABSTRACT

A light-sensitive silver halide photographic material comprising a m-aminophenol type coupler of the structure particularly defined therein is disclosed, which can successfully yield an excellent image stable against oxidation.

4 Claims, No Drawings

LIGHT-SENSITIVE SILVER HALIDE PHOTOGRAPHIC MATERIALS

This is a continuation in part application of Ser. No. 726,635 filed on Sept. 27, 1976, now abandoned, and claims the priority of Japanese application 118480/1975 filed on Sept. 30, 1975.

This invention relates to a novel light-sensitive silver halide photographic material. More particularly, the invention is concerned with a light-sensitive silver halide photographic material comprising a photographic couplers capable of giving an excellent neutral black dye image.

In an ordinary black-and-white photography, a latent image is formed in a light-sensitive silver halide photographic material by exposing said photographic material to light, the latent image thus formed is developed by means of a developer containing a black-and-white developing agent (such agent is well known to the industry concerned, for example, as Metol, phenidone, pyrogallol or hydroquinone) and metallic silver thereby formed on the exposed portion of the photographic material is utilized as a photographic image. In this black-and-white photography, the developing agent thereby oxidized is quickly removed outside the photographic material. Then, if the thus oxidized developing agent is utilized as a material capable of forming a black dye image, there can be expected further an improvement in density or in speed.

For such purpose as mentioned above, various methods have heretofore been proposed. For instance, West German Pat. Nos. 492,518 and 537,923 disclose a process for forming black dye images by carrying out color development by use of an adequate mixture of such couplers as yellow, magenta and cyan couplers which can be used in common color photography. In this process, however, it is difficult to obtain neutral black dye images for all density region for such reasons that these three couplers are different from one another in their rate of coupling with an oxidized color developing agent, for example, a p-phenylenediamine type color developing agent or a p-aminophenol type color developing agent. Further, West German Pat. No. 1,158,836 discloses a process for forming black dye images by use of 4-aminopyrazolinobenzimidazole as a developing agent, wherein the oxidation product of the developing agent is condensed with an active methylene compound. According to this process, however, it is practically difficult to obtain a substantially neutral black dye image having a sufficient density.

Furthermore, processes for forming black dye images by means of developer couplers are disclosed, for example in British Pat. No. 1,210,417 and U.S. Pat. No. 3,615,509. The processes are intended to obtain a substantially black dye image having a sufficiently high density by developing a silver halide emulsion by use of a developing agent which has in the molecule a coupler moiety consisting of phenol and developing agent moiety consisting of p-aminophenol, thereby forming a polymerized dye in the exposed portion and then subjecting the polymerized dye to chelation by treatment with an alkali bath or a copper chelate bath.

Even in these processes, there remain problems such as unstability of the processing solution, complexity in handling because of adding use of a copper chelate bath, unstability of the copper chelate bath, and insufficient stability of the image.

Still further, U.S. Pat. No. 3,674,490 discloses a process for forming quinone type black dye images, according to which the silver image once obtained by an ordinary black-and-white photographic treatment is allowed to oxidatively couple on the silver image portion with an aromatic hydroxyamino compound, utilizing hydrogen peroxide as a reaction catalyst. In this process, however, in addition to the fact that the process requires additional processing baths, it is difficult to obtain black dye images having a sufficient density under usually employed processing conditions.

Accordingly, a primary object of the present invention is to provide a light-sensitive silver halide photographic material capable of forming thereon a neutral black dye image of high density.

A second object of the present invention is to provide a light sensitive silver halide photographic material capable of forming thereon a neutral black dye image of high density which is free from stain and excellent in image stability.

A third object of the present invention is to provide a light-sensitive silver halide photographic material capable of forming thereon a neutral black dye image by subjecting said photographic material to a color process using a primary aromatic amine type color developing agent.

A fourth object of the present invention is to provide a light-sensitive silver halide photographic material containing a photographic coupler, which photographic material is capable of forming thereon a neutral black dye image without subjecting said photographic material to such a special image stabilization treatment as disclosed in U.S. Pat. Nos. 3,615,509 or 3,674,490.

Other objects of the present invention will become apparent from the description and working examples that follow.

It has now been found that the above-mentioned objects of the present invention can be accomplished by incorporating a black dye image forming coupler represented by the following general formula into a light-sensitive silver halide photographic material.

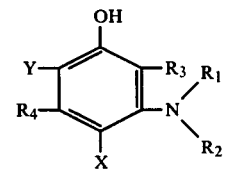

wherein $R_1$ and $R_2$ individually represent a hydrogen atom, an alkyl group, an aralkyl group, an aryl group or an alkenyl group, $R_3$ and $R_4$ individually represent a hydrogen atom, a halogen atom, hydroxyl, an alkyl group, an alkoxy group, an alkylamido group, an arylamido group, an alkylsulfonamido group or an arylsulfonamido group, and X and Y individually represent a hydrogen atom, a halogen atom (e.g. chlorine, bromine or the like) or a group capable of being split-off on the coupling reaction with an oxidation product of a primary amine type color developing agent (hereinafter called simply a "split-off group") or one of X and Y is hydroxyl, mercapto, amino, an alkylamino group or an arylamino group, and the other is a hydrogen atom, a halogen atom or a split-off group as defined above.

By the alkyl group represented by $R_1$ as well as by $R_2$ in the above-mentioned general formula is meant preferably an alkyl groups of 1 to 32 carbon atoms, more preferably an alkyl group of 1 to 22 carbon atoms, which alkyl group may be either straight chained or branched or which may be substituted. Typical examples of alkyl in the alkyl group include, for example, methyl, ethyl, isopropyl, n-butyl, n-dodecyl, n-octadecyl, sec-octadecyl and n-docosyl. As substituents of substituted alkyl in the alkyl group, there may optionally be selected any substituent. Preferably, however, there may be mentioned, for example, hydroxyl, carboxyl, sulfo, an alkylcarbamoyl group, an alkylsulfamoyl group, an arylcarbamoyl group, an arylsulfamoyl group, an alkoxycarbonyl group, an alkoxysulfonyl group, an aryloxycarbonyl group, an aryloxysulfonyl group, an alkoxy group, an aryloxy group, an alkylamido group and an arylamido group, an alkyleneformamido group, an arylsulfonamido group.

By the aralkyl group represented by the aforesaid $R_1$ and $R_2$ are meant such groups in which the carbon number of the alkylene chain connecting the N atom of a compound of the aforesaid general formula to the aryl moiety of said aralkyl group is preferably from 1 to 32, more preferably from 1 to 12, and said aryl moiety is preferably phenyl. Examples of the aralkyl group include, for example, benzyl, phenetyl β-naphthylmethyl, phenylheptyl and the like. As substituents of the substituted aralkyl group, there may optionally be selected any substituent. Preferably, however, there may be mentioned, for example, hydroxyl, carboxyl, a halogen atom (e.g. chlorine, bromine and the like), an alkyl group, an alkylamido group, an arylamido group, an alkylsulfonamido group and an arylsulfonamido group.

By the aryl group represented by the aforesaid $R_1$ and $R_2$ is meant preferably phenyl group. As substituents of the substituted phenyl included in the phenyl group, there may be optionally selected any substituent. Preferably, however, there may be mentioned, for example, a halogen atom (e.g. chlorine, bromine or the like), an alkylamido group, an arylamido group, an alkylsulfonamido group and an arylsulfonamido group.

By the alkenyl group represented by the aforesaid $R_1$ and $R_2$ is meant preferably a straight chained or branched alkenyl group of 3 to 22 carbon atoms, which may be of cyclic structure. Examples of the alkenyl group include, for example, allyl, octenyl, cyclohexenylethyl, 5,9-dimethyl-9-dodecenyl and 9-octadecenyl. As substituents of substituted alkenyl included in the alkenyl group, there may be mentioned preferably a halogen atom (e.g. chlorine, bromine or the like).

The alkyl moieties of the alkyl carbamoyl group, the alkyl sulfamoyl group, the alkoxycarbonyl group and the alkoxy sulfonyl group which moieties were mentioned as the substituent in the alkyl group represented by the aforesaid $R_1$ and $R_2$ means preferably straight chained or blanched alkyl of 1 to 22 carbon atoms. Said alkyl moiety may have a substituent.

AS the alkyl moieties, there may be mentioned, for example, methyl, ethyl, tert-butyl, octyl, n-octadecyl, sec-octadecyl, n-docosyl, 1-(n-octadecylcarbamoyl)ethyl, 2-(2-sulfooctadecanamido)ethyl, octadecyl succimidopropyl, 2-(N-octadecyl-N-carboxymethylaminoacetamido)ethyl, n-dodecyloxymethoxypropyl, 2,4-di-tert-amylphenoxybutyl, 3-pentadecylphenoxypropyl, and the like.

By an aryl moiety of the substituent of the alkyl group represented by the aforesaid $R_1$ and $R_2$, i.e. an arylcarbamoyl group, an arylsulfamoyl group, an aryloxycarbonyl group or an aryloxysulfonyl group, is meant preferably phenyl or naphthyl, more preferably, phenyl. As the aryl moiety, there may be mentioned, for example, phenyl, naphthyl, p-dodecylphenyl, m-pentadecylphenyl, o-tetradecyloxyphenyl, p-octadecyloxyphenyl, 2-methoxy-5-tetradecyloxycarbonylphenyl, 3,4-di-n-butyloxycarbonylphenyl, p-tert-butylphenoxyphenyl, m-lauroylamidophenyl, m-dodecylbenzenesulfonamidophenyl, 4-lauroylamidonaphthyl, 5-octadecyloxynaphthyl, 2-chloro-5-(2,4-di-tert-amylphenoxybutylamido)phenyl and the like.

An alkyl moiety of the alkoxy group previously described as the substituent of the alkyl group represented by the aforesaid $R_1$ and $R_2$, preferably includes straight chained or branched alkyl moieties of 1 to 22 carbon atoms, which alkyl moieties may further be substituted. As the alkyl moiety, there may be mentioned, for example, methyl, propyl, heptyl, n-dodecyl, n-octadecyl, p-tert-butylphenoxyethyl, p-octadecylphenoxyethyl, dodecyloxyethyl and the like.

By an aryl moiety of the aryloxy group previously mentioned as the substituent of the alkyl group represented by the aforesaid $R_1$ and $R_2$, is meant preferably substituted or unsubstituted phenyl. As the substituted phenyl, there may be mentioned, for example, p-dodecylphenyl, p-lauroylamidophenyl, p-tert-butylphenoxyphenyl, m-octadecylsulfonamidophenyl.

By the alkylamido group mentioned previously as the substituent of the alkyl, aralkyl or aryl group represented by the aforesaid $R_1$ and $R_2$ is meant preferably alkanoic acid amido group of 1 to 22 carbon atoms which may further be substituted. As an alkyl amido, there may be mentioned, for example, butanamido, octanamido, dodecanamido, hexadecanamido and the like. As the substituted alkyl amido, there may be mentioned, for example, m-pentadecylphenoxyacetamido, 2,4-di-tert-amylphenoxybutanamido, p-tert-amylphenoxycarbonylpropanamido, m-decyloxyphenoxyacetamido, 2-n-butoxydodecanamido and the like.

By the aryl amido group mentioned previously as the substituent of the alkyl, aralkyl or aryl group represented by the aforesaid $R_1$ and $R_2$ is meant preferably a benzamido or a naphthamido group, more preferably a benzamido group. As an arylamido, there may be mentioned, for example, benzamido, α-naphthamido and the like. As substituted aryl amido, there may be mentioned preferably, for example, p-methylbenzamido, p-tert-butylbenzamido, m-lauroylamidobenzamido, o-dodecyloxybenzamido, m-(p-tert-amylphenoxy)benzamido and the like.

By the alkylsulfonamido group mentioned previously as the substituent of the alkyl, aralkyl or aryl group represented by the aforesaid $R_1$ and $R_2$ is meant preferably straight chained or branched alkylsulfonamido group of 1 to 22 carbon atoms, which may further be substituted.

As an alkylsulfonamido, there may be mentioned, for example, methanesulfonamido, butanesulfonamido, 2-methylpropane-2-sulfonamido, dodecane-1-sulfonamido, docosane-1-sulfonamido and the like. As substituted alkylsulfonamido, there may be mentioned, for example, N-methyllauroylamidoethanesulfonamido, N-phenyloctadecanamidoethanesulfonamido, lauroylamidoethanesulfonamido and the like.

By the arylsulfonamido group mentioned previously as the substituent of the alkyl, aralkyl or aryl group represented by the aforesaid $R_1$ and $R_2$ is meant preferably a phenylsulfonamido or a naphthylsulfonamido groups, which may further be substituted. As an arylsulfonamido group, there may be mentioned preferably, for example, benzenesulfonamido, naphthalenesulfonamido and the like. As a substituted arylsulfonamido, there may be mentioned, for example, toluenesulfonamido, p-octadecanamidobenzenesulfonamido, p-dodecylbenzenesulfonamido, 4,8-diisopropylnaphthalene-2-sulfonamido, 3-methoxy-6-octadecanamidobenzenesulfonamido and the like.

By the alkyl group mentioned previously as the substituent of the aralkyl group represented by the aforesaid $R_1$ and $R_2$ is meant preferably straight chained or branched alkyl of 1 to 22 carbon atoms which may further be substituted, for example, preferably by methyl, ethyl, dodecyl and the like.

By the alkyl group represented by the aforesaid $R_3$ and $R_4$ is meant preferably alkyl of 1 to 22 carbon atoms, more preferably alkyl of 1 to 4 carbon atoms, which may be either straight chained or branched. For example, there may be mentioned methyl, ethyl, tert-butyl and the like.

By the alkoxy group represented by the aforesaid $R_3$ and $R_4$ is meant preferably an alkoxy of 1 to 22 carbon atoms. There may be mentioned preferably, for example, methoxy, ethoxy, butoxy, dodecyloxy, n-octadecyloxy, sec-octadecyloxy and the like.

By the alkylamido group represented by the aforesaid $R_3$ and $R_4$ is meant preferably an alkylamido of 1 to 22 carbon atoms, which may be either straight chained or branched. As the alkylamino, there may be mentioned, for example, preferably acetamido, propionamido, hexadecanamido and the like.

By the alkylsulfonamido group represented by the aforesaid $R_3$ and $R_4$ is meant preferably alkylsulfonamido of 1 to 22 carbon atoms, which may be either straight chained or branched. As the alkylsulfonamido, there may be mentioned, for example, preferably methanesulfonamido, propanesulfonamido, sec-butanesulfonamido, n-dodecansulfonamido, n-octadecanesulfonamido and the like.

By the arylamido or arylsulfonamido group represented by the aforesaid $R_3$ and $R_4$ is meant those having the same meaning as in the arylamido or arylsulfonamido group mentioned previously as the substituent of the alkyl, aralkyl or aryl group represented by the aforesaid $R_1$ and $R_2$.

By the split off group represented by the aforesaid X and Y is meant preferably a sulfo (—SO$_3$H) or its salts, a carboxyl (—COOH) or its salts, an alkoxy group, an aryloxy group, an alkylcarbonyloxy group, an alkylsulfonyloxy group, an arylcarbonyloxy group, an arylsulfonyloxy group, an alkylcarbamoyloxy group, an arylcarbamoyloxy group, an alkylamido group, an arylamido group, an alkylsulfonamido group, an arylsulfonamido group, 5- or 6-membered imido group, an arylthio group, an arylseleno group, an arylsulfonyl group, an arylazo group and a 5- or 6-membered heterocyclic thio group containing in the molecular structure 1 to 4 nitrogen atoms.

As an alkyl moiety of the alkoxy group defined as the aforesaid split off group, there may be mentioned preferably straight chained or branched alkyl moiety of 1 to 8 carbon atoms, preferably 1 to 4 carbon atoms, which may further be substituted. The alkyl moiety includes methyl, ethyl, isopropyl, chloroethyl, butoxycarbonylmethyl, β-hydroxyethoxycarbonylmethyl, m-hexadecanamidophenoxycarbonylmethyl, β-methoxyethoxycarbonylpropyl, iso-propylcarbamoylmethyl, n-dodecylcarbamoylmethyl, m-dodecanamidophenylcarbamoylpropyl, m-hexadecanamidophenoxycarbonylmethyl, o-dodecyloxyphenylcarbamoylmethyl and the like.

By the aryloxy group defined as the aforesaid split off group is meant preferably phenyloxy group which may further be substituted. As the aryloxy group, there may be mentioned, for example, phenoxy. As substituents of the substituted aryloxy, there may be mentioned, for example, carboxyl or its salts, sulfo or its salts, halogen atom and the like.

The alkyl moiety of this alkylcarbonyloxy group defined as the split off group includes preferably straight chained or branched alkyl moiety of 1 to 22 carbon atoms which may further be substituted. The alkyl moiety includes preferably methyl, ethyl, tert-butyl, n-dodecyl, n-docosyl and the like. Substituents of the alkyl moiety having a substituent are preferably halogen atom (e.g. fluorine, chlorine, bromine and the like).

By the arylcarbonyloxy group defined as the split off group is meant preferably phenylcarbonyloxy group. The arylcarbonyloxy group defined as the split off group includes preferably phenylcarbonyloxy which may further be substituted. The arylcarbonyloxy group includes preferably phenylcarbonyloxy group and the like. As substituents of a substituted arylcarbonyloxy, there may be mentioned, for example, an alkyl group, an alkylamido group and the like. The alkyl group is preferably an alkyl, for example, methyl, tert-butyl and the like. The alkylamido group includes, for example, dodecanamido, 2,4-di-tert-amylphenoxyacetamido and the like.

An alkyl moiety of the alkylsulfonyloxy group defined as the split off group includes preferably straight chained or branched alkyl moiety of 1 to 22 carbon atoms which may further be substituted. An unsubstituted alkyl moiety includes methyl, tert-butyl, n-dodecyl, n-docosyl and the like. As substituents of the alkyl moiety having a substituent, there may be mentioned any groups as selected. Preferably, however, there may be mentioned alkylamido group, for example, such alkylamido as lauroylamido, N-methyllauroylamido and the like.

An aryl moiety of the arylsulfonyloxy group defined as the split off group includes preferably phenyl group which may further be substituted. An unsubstituted aryl moiety includes, for example, phenyl and the like. As substituents of the aryl moiety having a substituent, there may be mentioned preferably, for example, alkyl of 1 to 22 carbon atoms.

By the alkylcarbamoyloxy group defined as the split off group is meant preferably alkylcarbamoyloxy of 1 to 4 carbon atoms.

By the arylcarbamoyloxy group defined as the split off group is meant preferably phenylcarbamoyloxy group. As the arylcarbamoyloxy group, there may be mentioned, for example, phenylcarbamoyloxy and the like. As a substituent of the substituted arylcarbamoyloxy, there may be mentioned, for example, a halogen atom, an alkoxy group, preferably an alkoxy (e.g. methoxy, ethoxy and the like), an alkylamido group, preferably alkylamido (e.g. propionamido, dodecamido and the like) and cyano.

As the alkylamido group defined as the split off group, there may be mentioned particularly preferably halogen-substituted alkylamido, for example, trichloroacetamido, trifluoroacetamido, heptafluoropropionamido, octafluoropentanamido and the like.

By the arylamido group defined as the split off group is meant preferably benzamido group, more preferably halogen-substituted benzamido, for example, pentachlorobenzamido, pentafluorobenzamido and the like.

By the alkyl and aryl moieties of the alkylsulfonamido group and arylsulfonamido group defined individually as the split off groups are meant the same as the alkyl and aryl moieties of the alkylsulfonyloxy group and arylsulfonyloxy group defined individually as the split off groups.

By the 5- or 6-membered imido group defined as the split off group are meant preferably a succiimido group and a gultalimido group, which may be substituted by alkyl group, preferably straight chained or branched alkyl of 1 to 22 carbon atoms, or which may form such condensation ring as in phthalimido group.

By the arylazo group defined as the split off group is meant preferably phenylazo group which is preferably phenylazo substituted with halogen atom or an alkyloxycarbonyl group of 1 to 22 carbon atoms, and the alkyl moiety of this alkyloxycarbonyl group may be further substituted. Examples of the arylazo group includes, for example, 2-chloro-5-{α-(dodecyloxycarbonyl)ethoxycarbonyl}phenylazo, o-octadecyloxycarbonylphenylazo and the like.

By the 5- or 6-membered heterocyclic thio group having in the molecular structure 1 to 4 nitrogen atoms defined as the split off group is meant such heterocyclic thio group as imidazole, triazole, tetrazole, oxazole, thiazole or thiadiazine group, and the heterocyclic moiety may form a condensation ring together with other unsaturated or saturated hydrocarbon. Examples of this thio group include, for example, 1-phenyltetrazolyl-5-thio, benztriazolylthio, benzoxazolylthio, benzthiazolylthio, 3-benzoyl-5-methyl-1,3,4-thiadiazine-2-yl-thio and the like.

Typical examples of the arylthio, arylseleno and arylsulfonyl groups defined as the split off groups are phenylthio, phenylseleno and phenylsulfonyl.

According to a preferred embodiment of the present invention, when the present compound of the general formula, in which X and Y are individually a hydrogen or halogen atom or a split off group, is used, the compound couples with 2 molecules of an oxidation product of an aromatic primary amine type color developing agent, thereby to form a pure black color dye different from an ordinary cyan color dye (this is, as is well known to the art, a dye resulting from coupling of a cyan coupler with one molecule of an oxidation product of an aromatic primary amine type color developing agent).

According to a more preferred embodiment of the present invention, moreover, quite favorable results can be obtained by the use of the compound of the general formula in which at least one of $R_1$ and $R_2$ is a hydrogen atom.

The black image forming coupler of the present invention is quite stable against oxidation since the coupler does not contain in the molecular structure a color developing agent moiety, and such instability to oxidation as previously described in the prior art couplers was not observed.

Representative examples of the m-aminophenol type coupler used in the present invention are shown below, but the black image forming couplers usable in the invention are not limited only to those as exemplified.

(1) N-Decyl-m-aminophenol

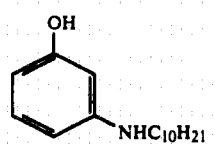

(2) N-Dodecyl-m-aminophenol

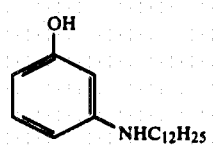

(3) N-Octadecenyl-m-aminophenol

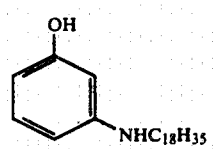

(4) N-Octadecyl-m-aminophenol

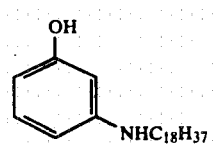

(5) 3-(p-Dodecylbenzylamino)phenol

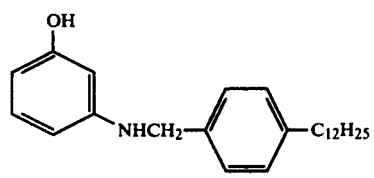

(6) 3-[4-(2,4-di-tert-Aminophenoxyacetamido)anilino]-phenol

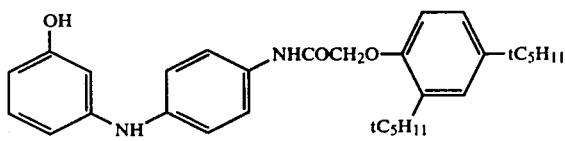

(7) 3-{[α-(Hexadecyloxycarbonyl)ethyl]amino}phenol

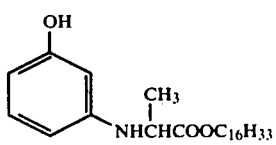

(8) N-[α-(Dodecylcarbamoyl)ethyl]-m-aminophenol

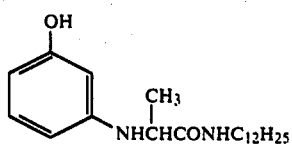

(9) N-[β-(Dodecylcarbamoyl)ethyl]-m-aminophenol

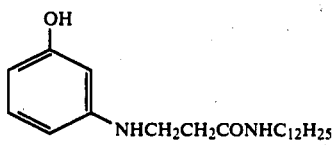

(10) N-{β-[2-Chloro-5-(2,4-di-tert-amylphenoxybutylamido)phenylcarbamoyl]ethyl}-m-aminophenol

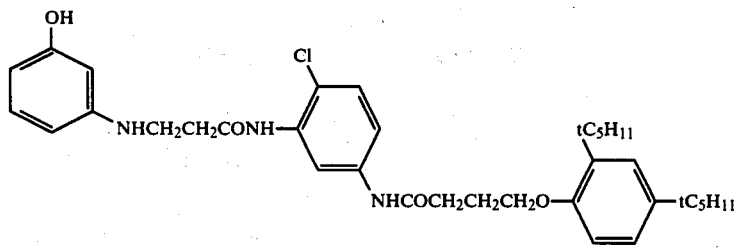

(11) N-(4-Lauroylamidophenethyl)-m-aminophenol

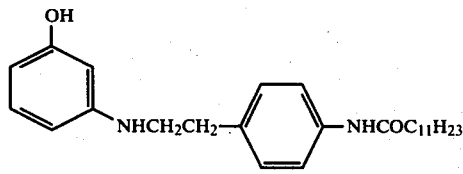

(12) N-{4-[α-(2,4-di-tert-Amylphenoxy)propionamido]-phenethyl}-m-aminophenol

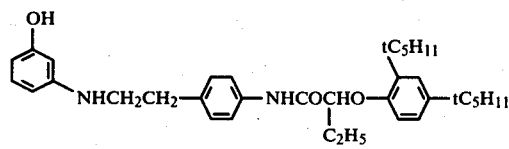

(13) 4-Chloro-N-octadecyl-m-aminophenol

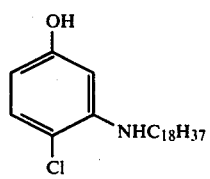

(14) 4-Sulfo-N-octadecyl-m-aminophenol

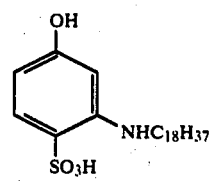

(15) N,N-Didodecyl-m-aminophenol

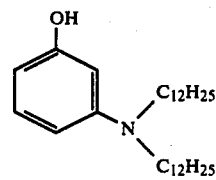

(16) N-Methyl-N-octadecyl-m-aminophenol

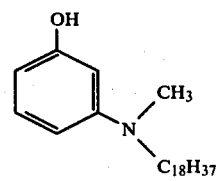

(17) N-{α-Carboxytridecyl}-m-aminophenol

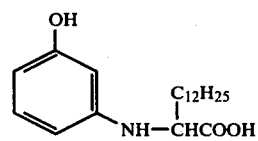

(18) N-{β-[2-Sulfo-5-(N-methyl-N-octadecylamino)phenylcarbamoyl]ethyl}-m-aminophenol

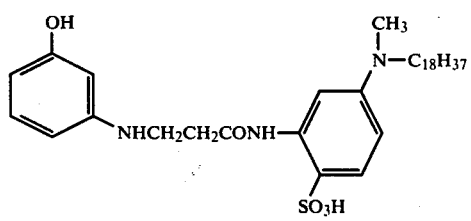

(19)
2-Pentafluorobenzamido-5-{2'-(3'-pentadecyloxy-
phenoxy)ethylamino}phenol

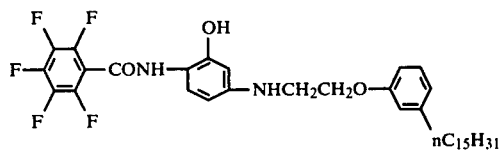

(20) 6-Chloro-N-octadecyl-m-aminophenol

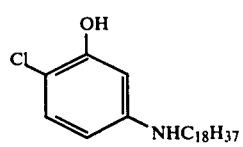

(21) 5-Ethoxy-3-hexadecyl-m-aminophenol

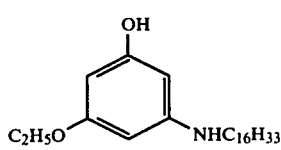

(22) 5-Dodecyloxy-m-ethylaminophenol

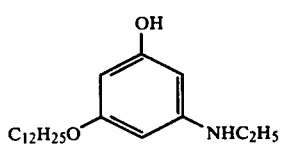

(23)
5-Hydroxy-3-{N-[α-(hexadecyloxycarbonylethyl-
]amino}phenol

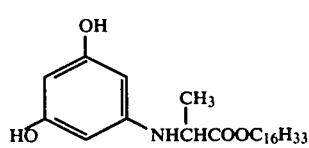

(24)
5-Benzoylamido-3-{α-(dodecylcarbamoyl)e-
thylamino}phenol

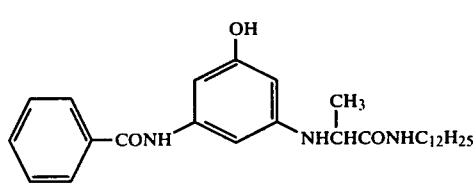

(25)
2-Acetamido-3-{α-(hexadecyloxycarbonyl)e-
thylamino}phenol

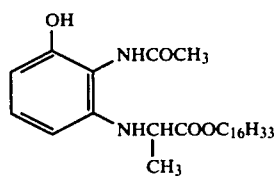

(26) 2-Benzenesulfonylamido-3-dodecylaminophenol

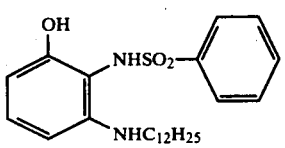

(27) 2-Palmiticacidamido-3-N-ethylaminophenol

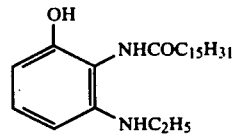

(28) 2,5-Dimethyl-3-N-octadecylaminophenol

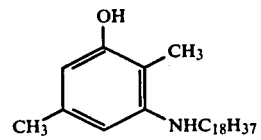

(29) 2-Hydroxy-4-chloro-5-N-octadecylaminophenol

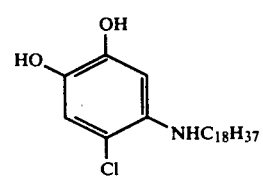

(30) 2,4,6-Trichloro-3-N-octadecylaminophenol

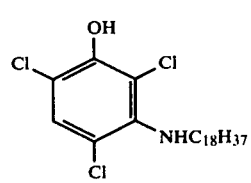

(31) 2,4-Disulfo-5-N-hexadecylaminophenol

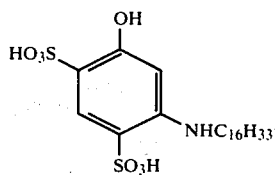

(32) 4-Phenylthio-3-N-octadecylaminophenol

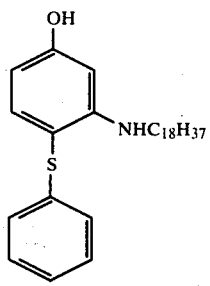

(33) 6-Phenylthio-3-N-octadecylaminophenol

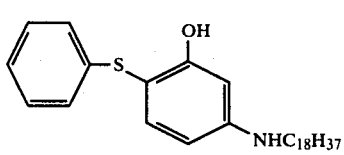

(34) 2,4-Diphenylthio-5-{4-(2,4-di-tert-amylphenoxyacetamido)anilino}phenol

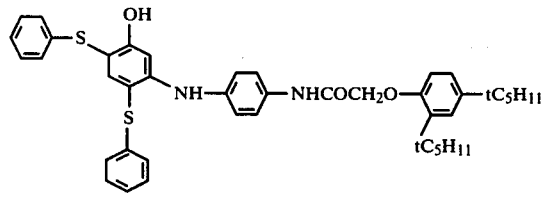

(35) 2-Chloro-4-phenylthio-5-[{β-(dodecylcarbamoyl)ethyl}amino]phenol

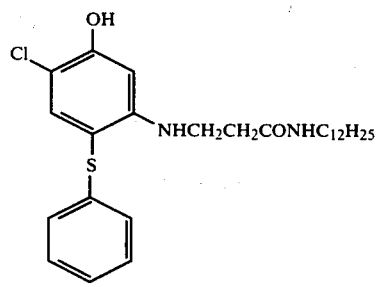

(36) 4-(1-Phenyltetrazolium-5-thio)-3-[β-(m-pentadecylphenoxy)ethylamino]phenol

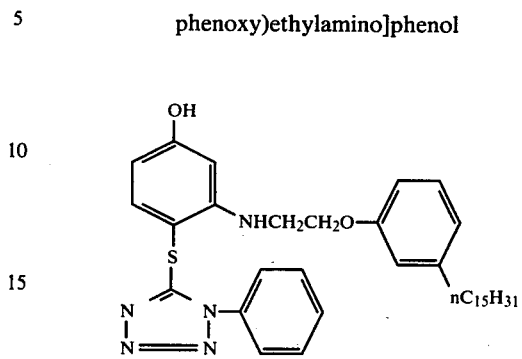

(37) 2-Mercapto-5-N-octadecylaminophenol

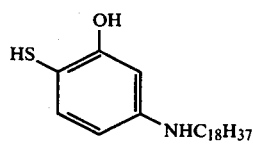

(38) 4-Phenylseleno-3-N-octadecylaminophenol

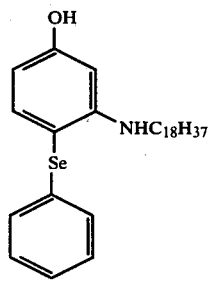

(39) 4-Ethoxy-3-N-octadecylaminophenol

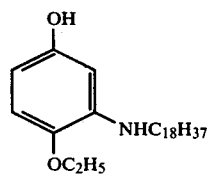

(40) 2-Chloroethoxy-5-N-octadecylaminophenol

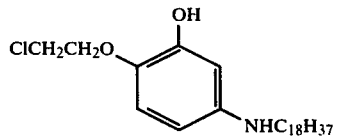

(41)
2-Chloro-4-(iso-propylcarbamoylmethoxy)-5-N-octadecylaminophenol

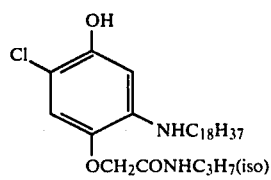

(42)
4-(iso-Propylcarbamoylmethoxy)-3-N-octadecylaminophenol

(43)
2,4-Dichloro-3-methoxy-5-N-hexadecylaminophenol

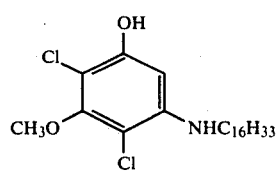

(44)
4-Buthoxycarbonylmethoxy-3-{[α-hexadecyloxycarbonyl)ethyl]amino}phenol

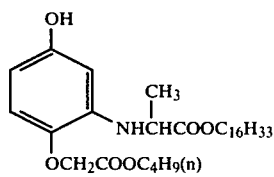

(45)
4-(p-Carboxyphenoxy)-3-{[α-(p-dodecylphenylcarbamoyl)ethyl]amino}phenol

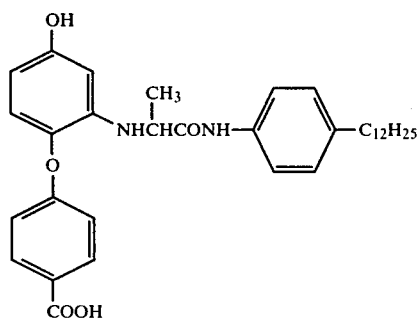

(46) 4-Benzoyloxy-3-N-dodecylaminophenol

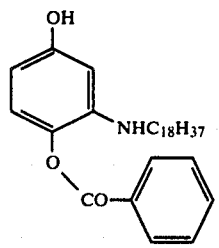

(47)
4-Acetoxy-3-[(O-hexadecyloxyphenylcarbamoyl)methylamino]phenol

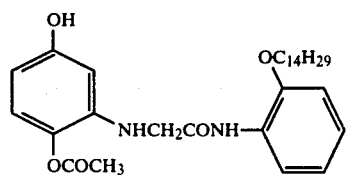

(48)
4-Perfluoropropyl-3-[(O-hexadecyloxyphenylcarbamoyl)methylamino]phenol

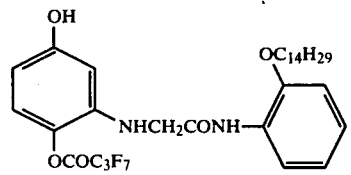

(49) 2-Phenoxy-5-N-octadecylaminophenol

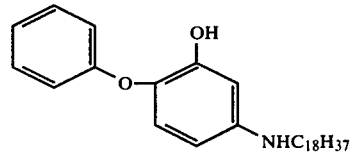

(50) 4-Benzensulfonyloxy-3-N-octadecylaminophenol

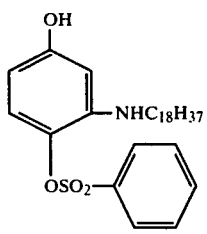

(51) 2-Chloro-4-benzensulfonyloxy-5-N-octadecylaminophenol

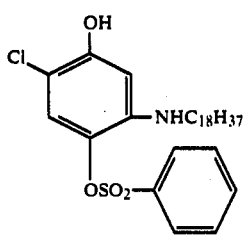

(52) 2-Succimido-5-N-hexadecylaminophenol

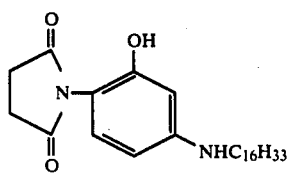

(53) 4-Phthalimido-5-N-hexadecylaminophenol

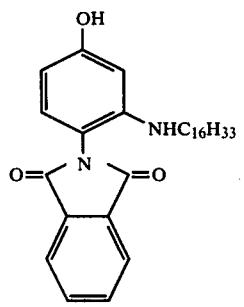

(54) 4-(p-Benzenesulfonylphenoxy)-3-N-octadecylaminophenol

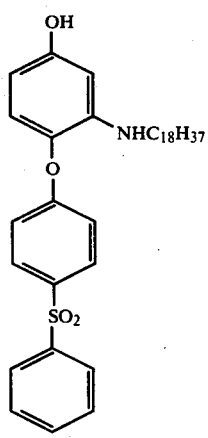

(55) 4-Phenylsulfonylamido-3-N-octadecylaminophenol

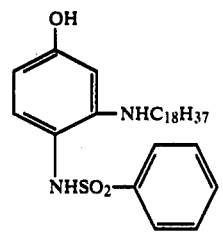

(56) 4-Methanesulfonylamido-3-N-octadecylaminophenol

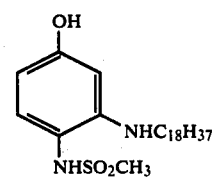

(57) 2-Phenylsulfonylamido-4-chloro-3-N-octadecylaminophenol

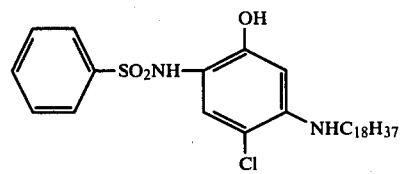

(58) 4-Trifluoroacetamido-3-N-dodecylaminophenol

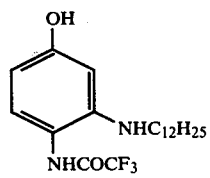

(59) 2-Amino-5-N-hexadecylaminophenol

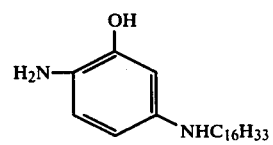

(60) 2-Anilino-5-N-octadecylaminophenol

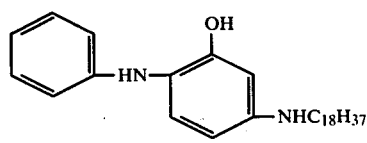

(61) 2-Ethylamino-5-N-hexadecylaminophenol

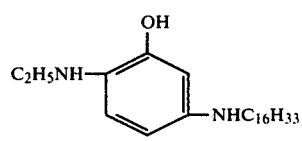

(62) 4-Phenylsulfonyl-3-N-octadecylaminophenol

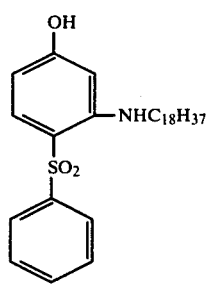

(63) 2-Octadecylsuccimido-5-γ-sulfopropylaminophenol sodium salt

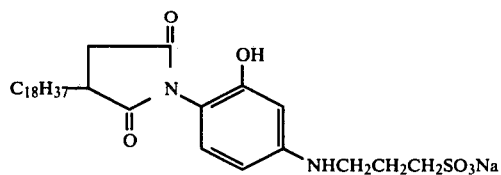

(64) 4-Dodecylcarbamoylmethoxy-3-N-ethylaminophenol

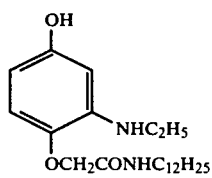

(65) 4-Dodecylcarbamoylmethoxy-3-N-(ω-sulfopropylamino)phenol sodium salt

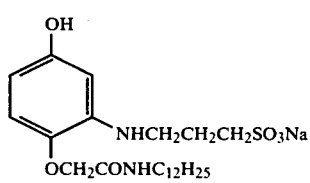

(66) 4-(p-Dodecylbenzenesulfonyloxy)-3-N-(ω-sulfopropylamino)phenol sodium salt

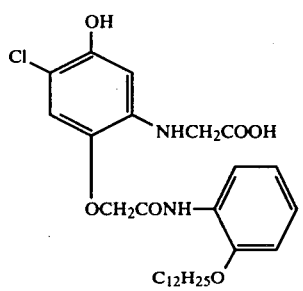

(67) 2-Chloro-4-(o-dodecylphenyl)carbamoylmethoxy-5-N-carboxymethylaminophenol

(68) 2-(m-Palmiticacidamidophenylsulfonamido)-5-(N-methoxycarbonylmethylamino)phenol

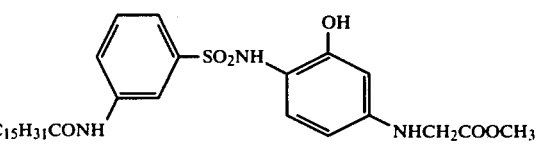

(69) 4-[2-Chloro-{5-[d-(dodecyloxycarbonyl)ethoxy]carbonyl}phenylazo]-3-(N-γ-sulfopropylamino)phenol

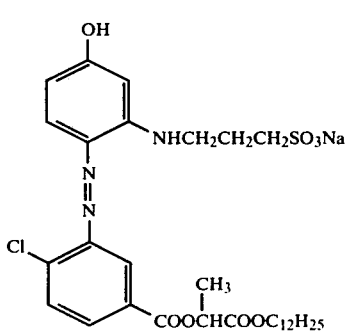

(70) 4-Dodecylcarbamoylmethoxy-3-aminophenol

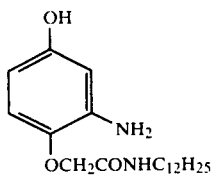

(71) 4-(p-Dodecylbenzensulfonyloxy)-3-N-ethylaminophenol

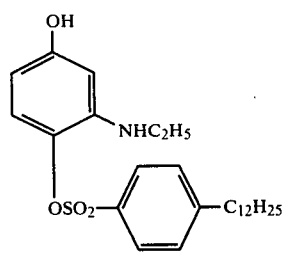

(72) 4-p-Methoxyphenylcarbamoyloxy-3-N-octadecylaminophenol

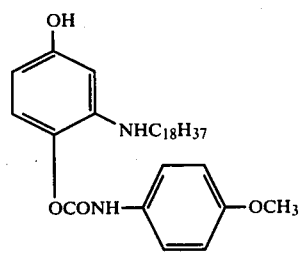

(73) N-[β-(Dodecylcarbamoyl)ethyl]-m-aminophenol

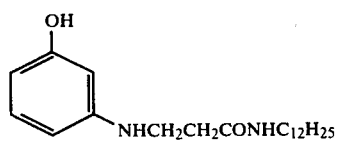

(74) N-(4-Lauroylamidophenethyl)-m-aminophenol

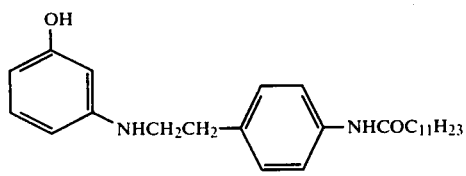

(75) 4-Chloro-3-(N,N-di-n-octadecylamino)phenol

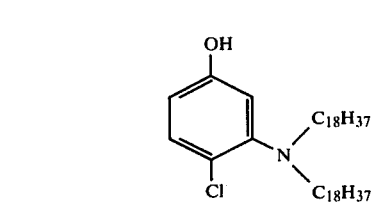

(76) 4-{(3-Lauroylamidophenyl)carbamoyloxy}-3-(N-γ-sulfopropyl)aminophenol

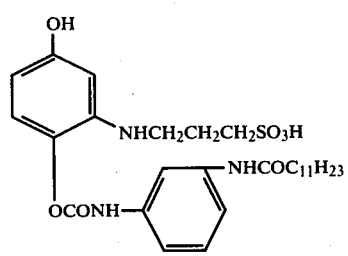

(77) 4-{(3-Lauroylamidophenyl)carbamoylmethoxy}-m-aminophenol

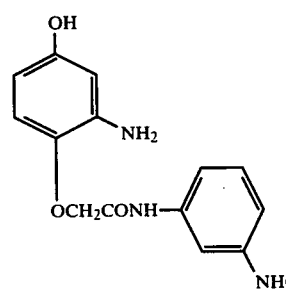

(78) 4-Dodecylbenzensulfonyloxy)-m-aminophenol

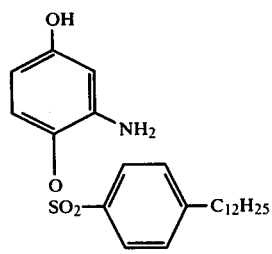

(79) 4-Dodecylbenzensulfonylamino)-m-aminophenol

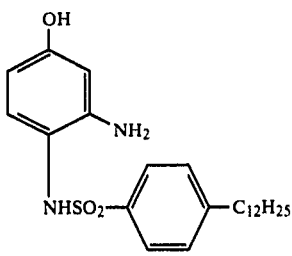

(80) 3-(γ-Sulfopropylamino)-4-(4'-dodecylphenylsulfonyloxy)phenol

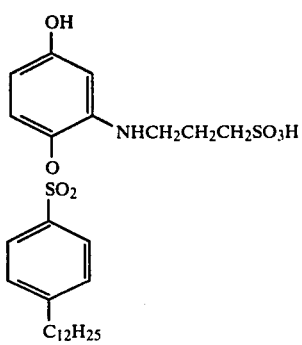

(81) 4-(Dodecylcarbamoylmethoxy)-3-(N-carboxymethyl-)aminophenol

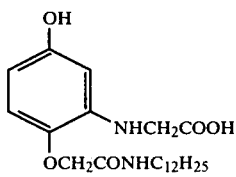

(82) 4-(Dodecylcarbamoylmethoxy)-3-(ethyloxycarbonylmethyl)-aminophenol

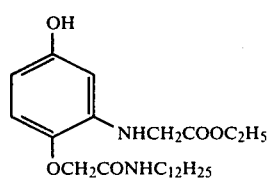

(83) 4-(3'-Dodecanamidoethoxycarbonylmethoxy)-3-(2-hydroxyethylamino)phenol

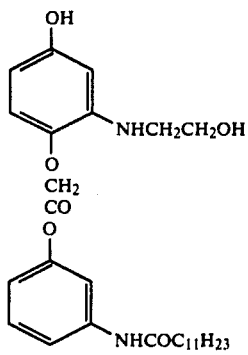

(84) 3-(4-Heptenylcyclohexylamino)phenol

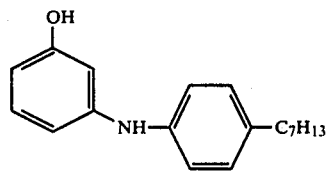

(85) 3-Octadecylamino-6-octafluoropentanamido phenol

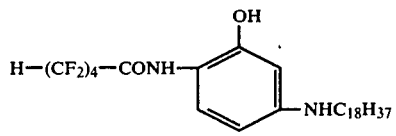

(86) 3-(2,4-di-tert-Amylphenoxybutylcarbamoylmethylamino)phenol

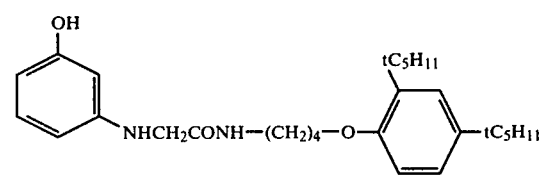

(87) 3-(γ-Dodecylsulfamoylethylamino)-4-{(2-methoxyethoxy)carbonylmethoxy}phenol

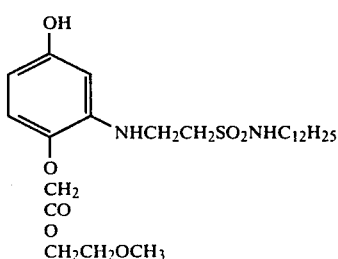

(88)

3-[{2'-(2''-Sulfooctadecanamido)ethyl}carbamoylmethylamino]phenol

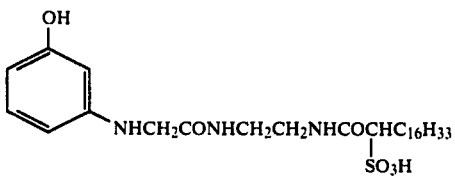

(89)

3-{4'-(4''-tert-Butylphenoxy)phenylcarbamoylethylamino}phenol

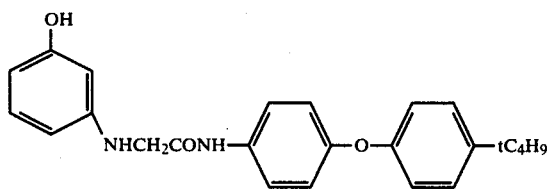

(90)

3-(3'-Dodecanamidophenylsulfamoylethylamino)-6-chlorophenol

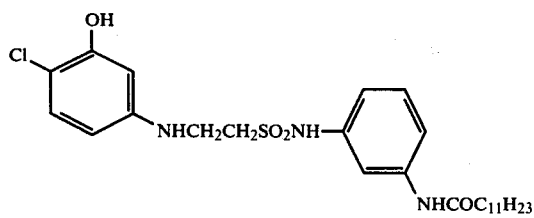

(91) 3-Octadecylamino-4-glutalimidophenol

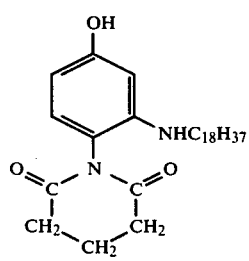

(92)

N-(5-Octadecyloxynaphthylcarbamoylethyl)-m-aminophenol

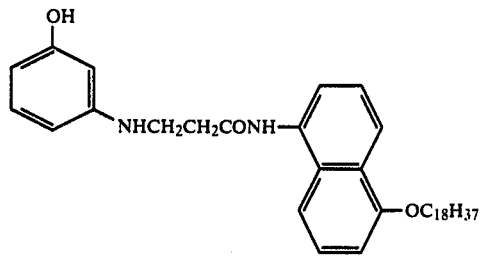

(93)

N-[2-{2'-(3''-Pentadecylphenoxy)ethoxysulfonyl}ethyl]-m-aminophenol

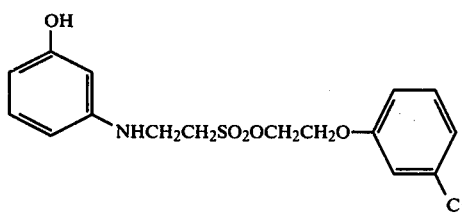

(94)

N-{2-(3'-Pentadecylphenoxy)ethoxycarbonylmethyl}-m-aminophenol

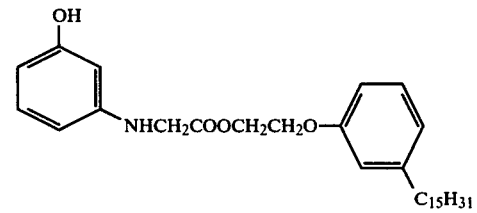

(95)

N-(3-Pentadecylphenoxycarbonylmethyl)-m-aminophenol

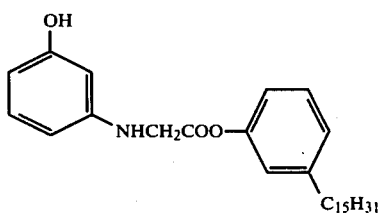

(96)
N-{2-(3'-Pentadecylphenoxysulfonyl)ethyl}-m-aminophenol

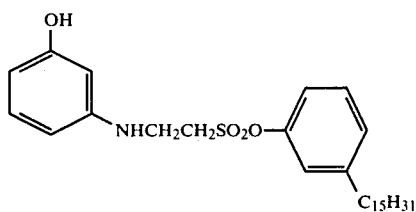

(97)
N-[2-{2'-(Dodecyloxy)ethoxy}ethyl]-m-aminophenol

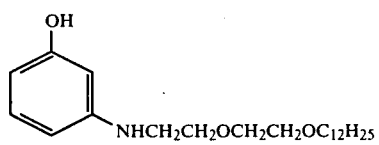

(98)
N-[2-{2'-(4''-tert-Butylphenoxy)ethoxy}ethyl]-m-aminophenol

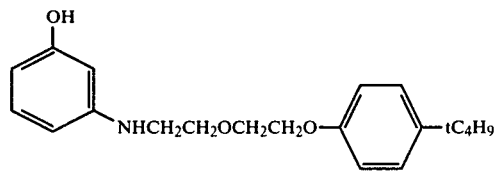

(99)
N-{2-(4'-Dodecanamidophenoxy)ethyl}-m-aminophenol

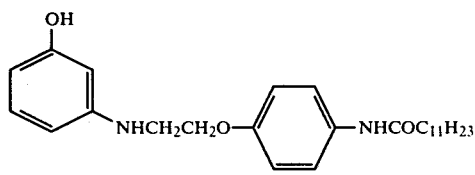

(100) N-{2-(4'-Dodecylphenoxy)ethyl}-m-aminophenol

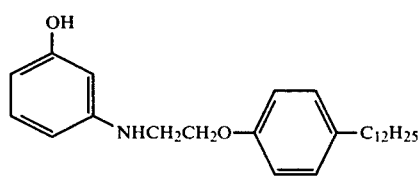

(101)
N-{2-(3'-Octadecansulfonamidophenoxy)ethyl}-m-aminophenol

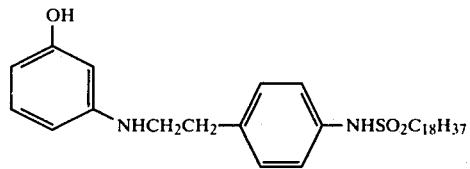

(102) 4-Chloro-3-(2'-dodecanamidoethylamino)phenol

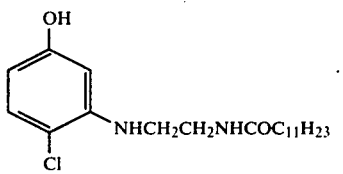

(103)
N-{2-(2',4'-di-tert-Amylphenoxyacetamido)ethyl}-m-aminophenol

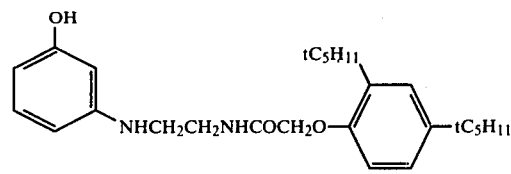

(104)
N-(4-Dodecansulfonamidophenetyl)-m-aminophenol

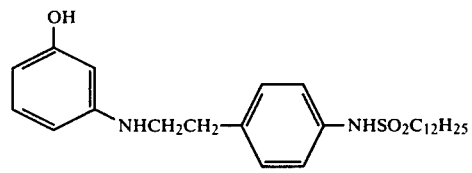

(105)
N-{2-(p-Dodecylbenzenesulfonamido)ethyl}-m-aminophenol

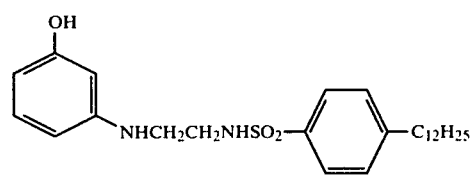

(106)
N-[2-{(1',5'-Diisopropyl-2-naphthalene)sulfonamido}ethyl)-m-aminophenol

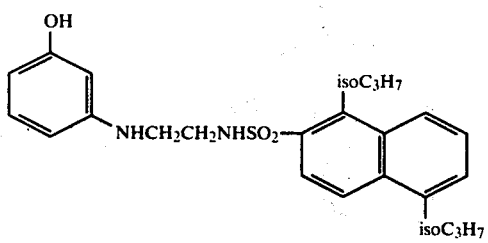

(107)
3-{(2'-Methylnaphthyl)methylamino}-5-dodecyloxyphenol

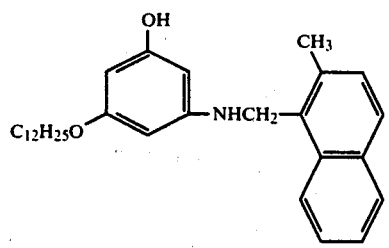

(108)
N-{2-(4'-tert-Butylbenzamido)ethyl}-m-aminophenol

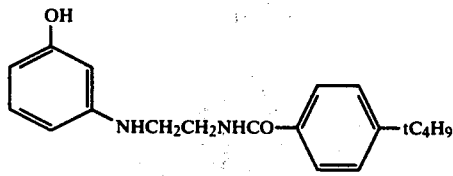

(109)
N-{2-(3'-Dodecanamidobenzamido)ethyl}-m-aminophenol

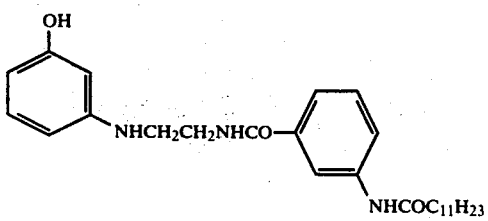

(110)
N-{2-(Dodecansulfonamido)ethyl}-m-aminophenol

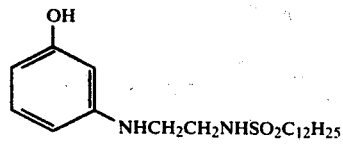

(111)
N-[2-{2'-(Dodecanamido)ethanesulfonamido}ethyl)-m-aminophenol

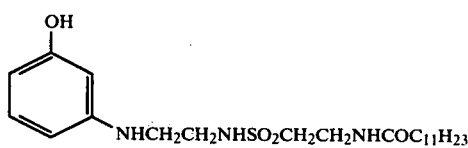

(112)
3-{5'-Chloro-2'-(2'',4''-di-tert-amylphenoxyacetamido)anilino}phenol

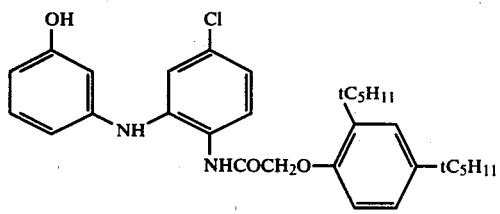

(113) 3-(4-Dodecylbenzenesulfonamidoanilino)phenol

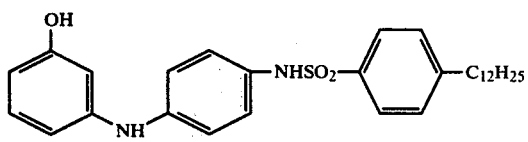

(114)
3-n-Octadecylamino-4-(benzimidazolyl-2-thio)phenol

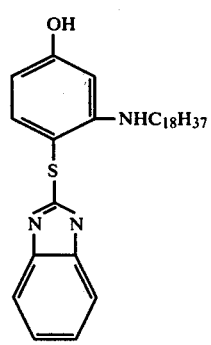

(115)

3-n-Octadecylamino-4-(4'-benzoyl-5'-methyl-1',3',4'-thiadiazinyl-2-thio)phenol

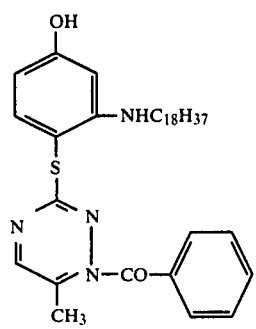

(116)

3-Dodecylcarbamoylmethylamino-4,6-di(benzoxazolyl-2-thio)phenol

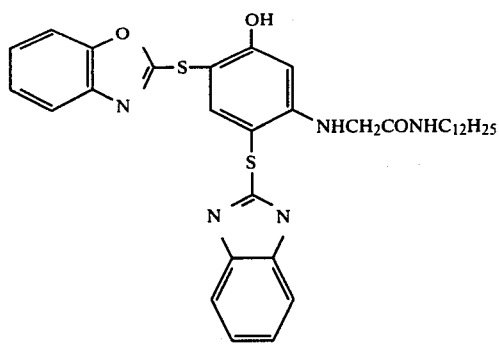

(117)

3-(Dodecylcarbamoylmethylamino)-4-(p-chlorophenylcarbamoyloxy)phenol

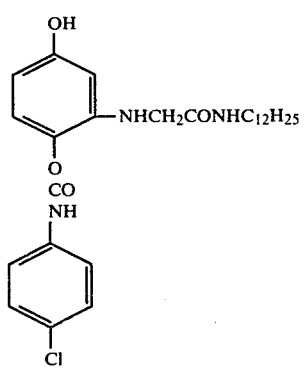

(118)

3-Amino-4-{3-(dodecanamido)benzoyloxy}phenol

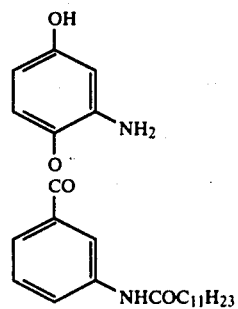

(119)

3-(γ-Sulfopropylamino)-4-hexadecylsulfonyloxyphenol

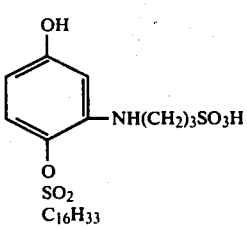

(120)

3-Ethylamino-4-{β-(N-phenyldodecanamido)ethylsulfonyloxy}phenol

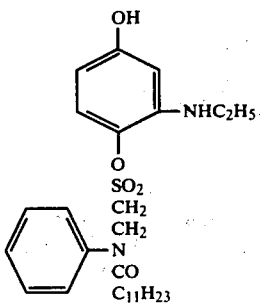

(121)

3-(γ-Sulfopropylamino)-4-(2-octadecyloxycarbonylphenylazo)phenol

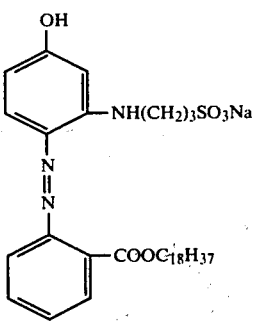

(122) 3-{β-(1-Cyclohexenyl)ethylamino}phenol

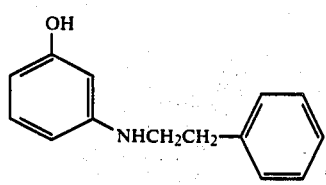

(123) 3-(Dodecenylamino)phenol

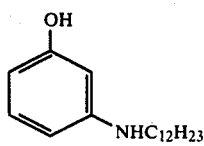

(124) 3-(4'-Hydroxyphenylcarbamoylmethylamino)-4-dodecylcarbamoylmethoxyphenol

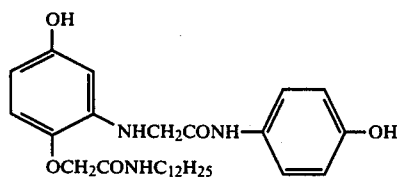

(125) 3-(4'-Sulfamoyl phenylcarbamoylmethylamino)-4-dodecylcarbamoylmethoxyphenol

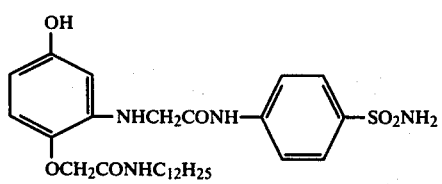

(126) 3-(3'-Carboxyphenylcarbamoylmethylamino)-4-(3''-dodecanamidophenylcarbamoylmethoxy)phenol

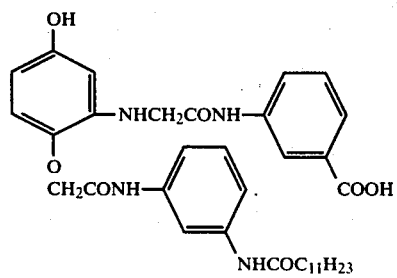

Concretely illustrated below are processes for the synthesis of representative couplers of the m-aminophenol type which are used in the present invention.

SYNTHESIS EXAMPLE 1

Preparation of 3-(p-dodecylbenzylamino)phenol

[Compound (5)]

Into 25 grams of m-aminophenol heated under reflux in 200 ml of alcohol was added dropwise over a period of 3 hours a solution of 30 g of p-dodecylbenzyl chloride in 100 ml of alcohol. After completion of the addition, the refluxing was continued for an additional 3 hours, the alcohol was then distilled off, the concentrate was dissolved in 300 cc of benzene, and the solution was washed twice with 300 cc of 10% hydrochloric acid. The benzene phase was washed with water, dried over sodium sulfate, and then the benzene was distilled off, whereby an oily brown liquid was obtained. The yield was 30 g, and the boiling point was 280° C.

SYNTHESIS EXAMPLE 2

Preparation of N-octadecyl-m-aminophenol

[Compound (4)]

Into 25 grams of m-aminophenol heated under reflux in 200 ml of alcohol was added dropwise over a period of 3 hours a solution of 33 g of octadecyl bromide in 100 ml of alcohol. After completion of the addition, the refluxing was continued for an additional 3 hours, the alcohol was then distilled off, the concentrate was dissolved in 300 cc of ethyl acetate, and the solution was washed twice with 300 cc of 10% hydrochloric acid. The ethyl acetate phase was washed with water, dried over sodium sulfate, and then the ethyl acetate was distilled off. Recrystallization from n-hexane gave white powdery crystals. The yield was 20 g and the melting point was 66°–68° C.

SYNTHESIS EXAMPLE 3

Preparation of 3-{[α-(hexadecyloxycarbonyl)ethyl]amino}phenol

[Compound (7)]

Into 25 g of m-aminophenol while heating under reflux in 200 ml of methanol was added dropwise over a period of 3 hours a solution of 37 g of hexadecyl α-bromopropionate in 100 ml of methanol. After completion of the addition, the refluxing was continued for an additional 3 hours, the methanol was then distilled off, the concentrate was dissolved in 300 cc of ethyl acetate, and the solution was washed twice with 300 cc of 10% hydrochloric acid. The ethyl acetate phase was washed with water, dried over sodium sulfate and was then concentrated. The concentrate was cooled with ice, whereby pale yellow crystals were deposited. The yield was 25 g and the melting point was 35°–40° C.

SYNTHESIS EXAMPLE 4

Preparation of N-[β-(dodecylcarbamoyl)ethyl]-m-aminophenol

[Compound (9)]

(a) Preparation of N-dodecyl-β-bromoethylamide

Into a solution of 34 g of β-bromopropionic acid chloride in 200 ml of benzene was added 15 g of anhydrous potassium carbonate, and the mixture was heated under reflux. To the refluxing mixture was added at a time 37 g of dodecylamine, and the refluxing was continued for an additional 4 hours. After completion of the refluxing, the reaction liquid was washed with water, and the benzene phase was dried over sodium sulfate and then concentrated. The concentrate was charged with n-hexane, whereby white powdery crystals were deposited, and the crystals were recrystallized from methanol. The yield was 35 g and and the melting point was 74°-76° C.

(b) Preparation of N-[β-(dodecylcarbamoyl)ethyl]-m-aminophenol

To 25 g of aminophenol heated under reflux in 200 ml of butanol was added dropwise over a period of 3 hours a solution of 32 g of N-dodecyl-β-bromoethylamide in 100 ml of butanol. After continuing the refluxing for an additional 3 hours, the butanol phase was washed twice with 300 cc of 10% hydrochloric acid, washed thoroughly with water, and then concentrated to obtain a brown oily liquid. The oily liquid was then cooled with ice, whereby crystals were deposited. The yield was 18 g and the melting point was below 40° C.

SYNTHESIS EXAMPLE 5

Preparation of 3-[4-(2,4-di-tert-amylphenoxyacetamido)anilino]phenol

[Compound (6)]

(a) Preparation of 3-(4-nitroanilino)phenol

A mixture of 32.4 g (0.3 mol) of m-aminophenol and p-nitrofluorobenzene (0.15 mol) was boiled under reflux for 10 days in 400 ml of water and then poured into dilute hydrochloric acid, followed by extraction with ethyl acetate, washing 2 to 3 times with dilute hydrochloric acid and then concentrated. The deposited crystals were washed with hot benzene, cooled and then filtered. The yield was 26 g and the melting point was 158°-160° C.

(b) Preparation of 3-(4-aminoanilino)phenol

20 Grams of 3-(4-nitroanilino)phenol was reduced under ordinary pressure in alcohol by the use of a palladium-carbon catalyst. After removing the catalyst by filtration, the alcohol was distilled off under reduced pressure and the residual solids were washed with benzene. The yield was 14 g, and melting point was 146°-149° C.

(c) Preparation of 3-[4-(2,4-di-tert-amylphenoxyacetamido)anilino]phenol

To a solution of 11 g (0.055 mol) of 3-(4-aminoanilino)phenol in glacial acetic acid was added 4.6 g of anhydrous sodium acetate. During agitation at room temperature, the mixture was charged with 17.1 g (0.055 mol) of 2,4-di-tert-amylphenoxyacetyl chloride at a temperature below 30° C. After continuing the agitation for an additional 30 minutes at that temperature, the mixture was poured into iced water, and the deposited crystals were filtered, followed by recrystallization with methanol. The yield was 20 g and the melting point was 150°-152° C.

SYNTHESIS EXAMPLE 6

Preparation of N-(4-lauroylamidophenethyl)-m-aminophenol

[Compound (11)]

(a) Preparation of 4-lauroylamidophenethyl bromide

A mixture of 8 g (0.04 mol) of 4-aminophenethyl bromide, 9 g of lauroyl chloride and 5 g of dimethylaniline was boiled under reflux for 30 minutes in 150 ml of acetonitrile. Subsequently, the acetonitrile was removed by distillation under reduced pressure, and the residue was then extracted with ethyl acetate, followed by washing with dilute hydrochloric acid. After drying over sodium sulfate, the ethyl acetate layer was concentrated under reduced pressure and the residual oily product was recrystallized from hexane. The yield was 12 g and melting point was 69°-70° C.

(b) Preparation of N-(4-lauroylamidophenethyl)-m-aminophenol

A mixture of 10 g (0.027 mol) of 4-lauroylphenethyl bromide and 6 g of m-aminophenol was boiled under reflux for 3 days in alcohol. After concentration of the alcohol, the concentrate was dissolved in ethyl acetate and the solution was washed with about 5% dilute hydrochloric acid, followed by water-washing. Subsequently, the ethyl acetate layer was dried over sodium sulfate, concentrated under reduced pressure and the residual oily product was recrystallized from benzene. The yield was 6 g and the melting point was 111°-112° C.

SYNTHESIS EXAMPLE 7

Preparation of 4-chloro-N-octadecyl-m-aminophenol

[Compound (13)]

According to the process described in Chemische Berichte, 26, 90; Chemische Berichte, 27, 195 or Beilstein, 6, (first edition), 239, 3-amino-4-chlorophenol was prepared to be used in the following synthesis:

In 800 ml of alcohol, 160 g of 3-amino-4-chlorophenol was heated under reflux for 30 hours with 187 g of octadecylbromide. Thereafter, the mixture was concentrated and 1 liter of ethyl acetate was added thereto. Insoluble substance (3-amino-4-chlorophenol hydrochloride) was eliminated by filtration and the ethyl acetate layer was washed three times with 1 liter of 5% hydrochloric acid and twice with 5% aqueous sodium bicarbonate solution. After being dried over sodium sulfate, the ethyl acetate layer was concentrated and the residual oil was recrystallized from 600 ml of hexane. The yield was 158 g and the melting point was 57°-59° C.

SYNTHESIS EXAMPLE 8

Preparation of 2,4,6-trichloro-3-(octadecylamino)phenol

[Compound (30)]

To a solution of 360 g of N-octadecyl-m-aminophenol in 1 liter of chloroform were added 450 g of sulfuryl chloride at room temprature while maintaining the temperature not exceeding over 20° C. After completion of the addition, the temperature was elevated to 40° C. and stirring was continued for 30 minutes. Chloroform was distilled off under reduced pressure and then extraction with 2 liters of ethyl acetate was effected. The ethyl acetate layer was washed with 5% aqueous sodium bicarbonate solution, dried over sodium sulfate and then concentrated. Recrystallization from 300 ml of hexane gave the title compound melting at 47°-49° C. in the yield of 200 g.

SYNTHESIS EXAMPLE 9

Preparation of 4-benzenesulfonylamido-3-(N-octadecylamino)-phenol (Compound (55))

According to the process described in Chemische Berichte, 26, 90 or Chemische Berichte, 27, 195, 3-nitro-4-aminophenol was prepared to be used in the following synthesis:

(1) Preparation of 1-benzenesulfonyloxy-4-benzenesulfonylamido-3-nitrobenzene

To a solution of 300 g of 3-nitro-4-aminophenol in pyridine were added 870 g of benzenesulfonium chloride and the solution was stirred at 50°–60° C. for one hour. The solution was poured into diluted hydrochloric acid/ice. The resulting crystal was washed with aqueous sodium bicarbonate solution and dried. The yield was 758 g.

(2) Preparation of 4-benzenesulfonylamido-3-nitrophenol

A solution of 536 g of 1-benzenesulfonyloxy-4-benzenesulfonylamido-3-nitrobenzene in methanol was heated under reflux. To the solution was added a solution of 310 g of potassium hydroxide in water and the solution was heated under reflux for further one hour. The reaction solution was poured into diluted hydrochloric acid/ice and extracted with ethyl acetate. After neutralization with sodium bicarbonate, the ethyl acetate layer was washed with water, dried over sodium sulfate and distilled to remove ethyl acetate. The residue was recrystallized from benzene to afford reddish brown crystal melting at 168°–170° C. in the yield of 274 g.

(3) Preparation of 4-benzenesulfonylamido-3-aminophenol

To a mixture of 260 g of 4-benzenesulfonylamido-3-nitrophenol, 700 cc of glacial acetic acid and 100 cc of water were added 320 g reduced iron and the mixture was stirred vigorously at 70°–80° C. After 1 hour, the mixture was poured into ice water and extracted with ethyl acetate. The extract was neutralized with sodium bicarbonate and the iron hydroxide precipitate was filtered. The ethyl acetate layer was washed with water, dried over sodium sulfate and distilled to remove ethyl acetate. The residue was recrystallized from ethyl acetate-benzene mixture to afford white powdery crystal melting at 177°–180° C. in the yield of 186 g.

(4) Preparation of 4-benzenesulfonylamido-3-(octadecylamino)phenol

A solution of 164 g of 4-benzenesulfonylamido-3-aminophenol in ethanol was heated under reflux and 68 g of octadecyl bromide were added to the solution. The resulting solution was further heated under reflux for 50 hours. Ethanol was removed by distillation and the concentrated solution was poured into water and adjusted to pH 3–4 with hydrochloric acid. The solution was extracted with ethyl acetate and ethyl acetate was distilled off. Thereafter, the residue was recrystallized from n-hexane. The yield was 120 g and the melting point was 113°–115° C.

SYNTHESIS EXAMPLE 10

Preparation of 4- or 6-phenylthio-3-octadecylaminophenol

[Compound (32)]

A solution of 370 g of N-octadecyl-m-aminophenol in 1.5 liters of carbon tetrachloride was cooled below 10° C. and to this solution was added under stirring a solution of phenylsulfenylchloride which had been prepared by dissolving 110 g of phenyl mercaptan in 200 ml of carbon tetrachloride and passing therethrough chlorine gas for 15 minutes, while maintaining the temperature below 10° C. Stirring was continued for 30 minutes and thereafter the solution was concentrated and extracted with 1 liter of ethyl acetate. The extract was washed twice with 500 cc of 5% sodium bicarbonate and dried over sodium sulfate. After removal of sodium sulfate, the ethyl acetate layer was concentrated, leaving oil which was crystallized from 1.5 liters of methanol-ethyl acetate mixed solvent (methanol: ethyl acetate = 5:1). The yield was 143 g and the melting point was 50°–51° C.

SYNTHESIS EXAMPLE 11

According to the process described in Chemische Berichte, 49, 1401, 3-nitro-4-benzoyloxyphenol was prepared and used for the syntheses of 4-(dodecylcarbamoylmethoxy)-3-aminophenol [Exemplified compound (70)] and sodium salt of 4-(dodecylcarbamoylmethoxy)-3-(γ-sulfopropylamino)phenol [Exemplified compound (65)] in the manner as disclosed below.

(1) Preparation of 1-benzoyloxy-3-nitro-4-(dodecylcarbamoylmethoxy)-benzene

In 500 ml of DMF, 195 L g of 3-nitro-4-benzoyloxyphenol were stirred with 240 g of N-dodecylbromoacetamide and 107 g of anhydrous potassium carbonate for 1 hour at 85°–90° C. The mixture was poured into 3 liters of ice water to which 100 ml of concentrated hydrochloric acid had been added. After extraction with 3 liters of ethyl acetate, the extract was washed twice with 1 liter of saturated aqueous sodium chloride solution. The ethyl acetate layer was dried over sodium sulfate and then concentrated. The residual crystal was recrystallized from 9 liters of methanol. The yield was 452 g and the melting point was 110°–111° C.

(2) Preparation of 3-nitro-4-(dodecylcarbamoylmethoxy)phenol

In 1 liter of methanol were suspended 275 g of 1-benzoyloxy-3-nitro-4-(dodecylcarbamoylmethoxy)benzene and 50 g of sodium hydroxide were added to the suspension at room temperature under stirring. After stirring for 30 minutes, the reaction solution was poured into 3 liters of ice water to which 150 ml of concentrated hydrochloric acid had been added. Extraction with 3 liters of ethyl acetate was effected and the ethyl acetate layer was washed three times with 3 liters of 5% aqueous sodium bicarbonate solution, dried over sodium sulfate and concentrated. The residual crystal was washed with acetonitrile. The yield was 203 g and the melting point was 150°–151° C. (acetonitrile).

(3) Preparation of 3-amino-4-(dodecylcarbamoylmethoxy)phenol

[Compound (70)]

In an autoclave, 190 g of 3-nitro-4-(dodecylcarbamoylmethoxy)phenol were subjected to pressure reduction (50 kg/cm²) with 500 ml of alcohol and 20 g of palladium/carbon. After the palladium/carbon catalyst was removed, concentration was effected and the residual oil was crystallized from 800 ml of acetonitrile. The yield was 120 g and the melting point was 78°–80° C.

(4) Preparation of sodium salt of 3-(γ-sulfopropylamino)-4-(dodecylcarbamoylmethoxy)-phenol

[Compound (65)]

In 300 ml of alcohol, 100 g of 3-amino-4-(dodecylcarbamoylmethoxy)-phenol and 40 g of propanesultone were stirred at room temperature for 30 hours. Said alcohol was distilled off under reduced pressure and the residual oil was dissolved in 500 ml of 5% aqueous sodium bicarbonate solution. To the resulting solution was added 300 ml of saturated aqueous sodium chloride solution and the solution was allowed to stand overnight. After neutralization with hydrochloric acid, the resulting crystal was filtered. The yield was 80 g and the melting point was above 200° C. with decomposition.

SYNTHESIS EXAMPLE 12

Preparation of 4-ethoxy-3-(N-octadecylamino)-phenol

[Compound (39)]

Similarly to Synthesis Example 11, 3-amino-4-ethoxyphenol was obtained, using p-toluenesulfonic acid ethyl ester in place of N-dodecyl-bromoacetoamide as used in Synthesis Example 11.

(1) Preparation of 3-palmitic acid amido-4-ethoxyphenol

With 500 ml of acetone, 100 ml of pyridine and 275 g of palmitic acid chloride, were boiled under reflux 153 g of 3-amino-4-ethoxy-phenol for 30 minutes. Acetone was distilled off and to the residue was added a mixture of 1 liter of ice water and 100 ml of hydrochloric acid. After extraction with 1 liter of ethyl acetate, the ethyl acetate layer was washed with water, dried over sodium sulfate and concentrated, leaving oil. The yield of crude oil was 430 g.

(2) Preparation of 3-(N-hexadecylamino)-4-ethoxyphenol [Compound (39)]

In 1 liter of tetrahydrofuran which had been dehydrated with sodium were dissolved 430 g of 3-palmitic acid amido-4-ethoxy-phenol (crude product obtained as above) and the resulting solution was added with stirring over 30 minutes to 1.5 liters of tetrahydrofuran to which 50 g of lithium aluminum hydride had been added. The mixture was then boiled under reflux for 2 hours and thereafter poured into ice water and neutralized with hydrochloric acid. Extraction with 4 liters of ethyl acetate was effected and the ethyl acetate layer was dried over sodium sulfate and concentrated. The residual crystal was recrystallized from n-hexane. The yield was 293 g and the melting point was 88°–90° C.

SYNTHESIS EXAMPLE 13

Preparation of sodium salt of 2-(octadecylsuccinimido)-5-(γ-sulfopropylamino)-phenol

[Compound (63)]

(1) Preparation of 2-octadecylsuccinimido-5-nitrophenol

In 3 liters of ethyl acetate and 50 ml of concentrated sulfuric acid were dissolved by heating 150 g of 2-amino-5-nitro-phenol and 350 g of octadecylsuccinate and the resulting solution was boiled under reflux for further 30 hours. Thereafter, the solution was cooled up to room temperature and washed twice with 2 liters of 10% hydrochloric acid and twice with 10% sodium carbonate solution. Then, ethyl acetated was distilled off and the residue was recrystallized from hexane to afford light yellow powdery crystal melting at 115°–120° C. in the yield of 153 g.

(2) Preparation of 2-octadecylsuccinimido-5-aminophenol

In 2 liters of ethanol were suspended 150 g of 2-octadecylsuccinimido-5-nitro-phenol and 7.5 g of palladium/carbon were added to the suspension, which was subjected to catalytic reduction with hydrogen gas at room temperature under normal pressure. After about 10 hours of reaction period of time, palladium/carbon was filtered off and ethanol was removed by distillation. The residue was recrystallized from benzene to give white powdery crystal melting at 85°–90° C. in the yield of 90 g.

(3) Preparation of sodium salt of 2-(octadecylsuccinimido)-5-(γ-sulfopropylamino)-phenol In 1.5 liters of ethanol, were dissolved by heating 90 g of 2-octadecylsuccinimido-5-amino-phenol and 24 g of propanesultone and the resulting solution was boiled under reflux for 35 hours. After completion of the reflux, ethanol was distilled off and 300 ml of 5% sodium bicarbonate solution was added to the concentrated solution. The solution was filtered and 75 ml of saturated sodium chloride solution was added to the filtrate. After neutralization with hydrochloric acid, the resulting crystal was collected by filtration. The yield was 27 g and the crystal was slowly decomposed above 200° C.

SYNTHESIS EXAMPLE 14

Preparation of sodium salt of 4-(2-chloro-{5-[α-(dodecyloxycarbonyl)-ethoxy]carbonyl}-phenyl-azo)-3-(γ-sulfopropylamino)-phenol

[Compound (69)]

(1) Preparation of 3-(γ-sulfopropylamino)-phenol

In 3 liters of ethanol were dissolved 330 g of m-amino-phenol and the resulting solution was boiled under reflux and to this solution were added 360 g of propanesultone all together. Continuation of the reflux yielded gradually white powdery crystal. After refluxing for 5 hours, the reaction solution was cooled with ice and the yielded white powdery crystal was collected by filtration and washed several times with ethanol. The yield was 146 g and the melting point was above 250° C.

(2) Preparation of sodium salt of 4-[2-chloro-{5-[α-(dodecyloxycarbonyl)-ethoxy]-carbonyl}-phenylazo]3-(γ-sulfopropylamino)-phenol To a solution of 204 g of 2-chloro-{5-[α-(dodecyloxycarbonyl)-ethoxy]-carbonyl}-aniline in 1 liter of acetone was added a mixed solution of 300 ml of concentrated hydrochloric acid and 300 ml of acetone. Further, 6 liters of a mixed solution of acetone:water=2:1 were added to the solution, which was then cooled with ice up to 0°–5° C. and further 4 liters of acetone were added thereto. To the resulting solution, a solution of 51 g of sodium nitrite in 300 ml of water was added in small portions while maintaining the reaction temperature at 0°–5° C. After completion of the addition, stirring was continued for 2 hours and 9 liters of a mixed solution of acetone:water=2:1 were added to the solution and further 6 liters of acetone were added. The solution was then stirred for 1 hour, elevating the temperature to 13° C. to form a diazo solution. To a solution of 1.2 g of 3-(γ-sulfopropylamino)-phenol in 1.8 liters of 10% sodium carbonate solution and 2.3 liters of acetone was added dropwise the diazo solution as prepared above at 0°–3° C. with stirring, while maintaining the reaction temperature at 0°–3° C. over about 2 hours. After completion of the addition, stirring was continued for further 2 hours and yellowish orange powdery crystal yielded was collected by filtration, washed several times with water and dried.

SYNTHESIS EXAMPLE 15

Preparation of 3-carboxymethylamino-4-n-dodecylcarbamoylmethoxyphenol

[Compound (81)]

(1) Preparation of 3-carboethoxymethylamino-4-N-dodecylcarbamoylmethoxyphenol [Compound (82)]

To a solution of 75 g of 3-amino-4-N-octadecylcarbamoylmethoxyphenol and 35 g of ethyl bromoacetate in 500 ml of ethanol was added 43 g of triethylamine, and the resulting mixture was refluxed on a water bath for 3 hours. After distilling off the ethanol under reduced pressure, the residual oily layer was dissolved in 500 ml of ethyl acetate, followed by thorough water-washing. After dehydrating the ethyl acetate layer on sodium sulfate, the layer was concentrated to dryness. The residual oily product was recrystallized from a hexanebenzene mixture to obtain the title compound. The yield was 42 g, and the melting point was 90°–92° C.

(2) Preparation of 3-carboxymethylamino-4-n-dodecylcarbamoylmethoxyphenol [Compound (81)]

To a suspension of 40 g of 3-carboethoxymethylamino-4-dodecylcarbamoylmethoxyphenol in 500 ml of methanol was added over 20 minutes a solution of 12 g of sodium hydroxide in 100 ml of water kept at below 20° C., and the mixture was stirred for 10 minutes to obtain a perfect solution. The resulting solution was poured into 2 liters of a 5% hydrochloric acid solution, whereupon pale green crystals were separated. The crystals were recrystallized from a water-methanol mixture to obtain the title compound. The yield was 32 g, and the melting point was 122°–125° C.

SYNTHESIS EXAMPLE 16

Preparation of 4-p-dodecylbenzenesulfonyloxy-3-(3-sulfopropyl)aminophenol

[Compound (80)]

(1) To a solution of 51.6 g of 2-nitro-4-benzoyloxyphenol (refer to Synthesis Example 11) in 200 ml of pyridine was added dropwise at below 20° C. 86 g of dodecylbenzenesulfonyl chloride, and the temperature of the mixture was elevated to 60° C. and stirring was continued for 1 hour. After cooling, the mixture was charged with 400 ml of concentrated hydrochloric acid and poured into 1 liter of ice-cold water, followed by extraction with 500 ml of ethyl acetate. The ethyl acetate layer was washed 2 times with a 5% aqueous sodium bicarbonate solution, dehydrated on magnesium sulfate and then concentrated to obtain a pale brown oily product (yield: 127 g).

Subsequently, this oily product was charged with 1.5 liters of methanol and further charged with stirring at below 13° C. with a solution of 20.6 g of potassium hydroxide in 50 ml of water. After 15 minutes, the reaction liquid was poured into 2 liters of ice-cold water charged with 150 ml of concentrated hydrochloric acid. The oily layer formed was separated and extracted with ethyl acetate, and the extract was washed with an aqueous sodium bicarbonate solution and then with brine. The ethyl acetate layer was dehydrated on magnesium sulfate and concentrated. The oily product thus resulted was substantially 4-p-dodecylbenzenesulfonyloxy-3-nitrophenol, which was used, as it was, in the subsequent reaction. The yield was 106 g.

(2) Preparation of 4-p-dodecylbenzenesulfonyloxy-3-aminophenol

[Compound (72)]

4-p-Dodecylbenzenesulfonyloxy-3-nitrophenol, which had been obtained in (1), was dissolved in 440 ml of a 90% acetic acid, and the solution was elevated with stirring in temperature to 60° C. To the solution was added in small portions 88 g of reduced iron powder in such a manner that the temperature of the solution may not exceed 85° C. After completion of the addition of iron powder, stirring was continued at 70°–80° C. for 2 hours. Subsequently, the resulting mixture was poured into ethyl acetate and neutralized with an aqueous sodium bicarbonate solution, followed by filtration. The ethyl acetate layer was separated from the filtrate and dehydrated on magnesium sulfate, and then the ethyl acetate is removed by concentration to obtain a reddish brown transparent oily product. This oily product was substantially 4-p-dodecylbenzenesulfonyloxy-3-aminophenol. The yield was 81 g.

(3) Preparation of 4-p-dodecylbenzenesulfonyloxy-3-(3-sulfopropyl)aminophenol

[Compound (80)]

To 43 g of 4-p-dodecylbenzenesulfonyloxy-3-aminophenol in a viscous state, which had been obtained in (2) was added at 100° C. 14 g of propane sultone to effect reaction. When stirring was continued, the reaction liquid gradually became viscous and after the lapse of about 1 hour the liquid became almost solid, followed by refluxing with addition of 200 ml of ethyl acetate. The solid syrup-like product then became loose to deposit fine white crystals. After cooling, the crystals were filtered and washed thoroughly with ethyl acetate. The yield was 26 g, and the crystals gradually decomposed at 180° C. and melted at 204°–205° C.

SYNTHESIS EXAMPLE 17

Preparation of 5-octafluoropentanamido-3-octadecylaminophenol

[Compound (85)]

To a solution of 116.6 g of 5-octafluoropentanamido-3-aminophenol hydrochloride and 100.0 g of octadecyl bromide in 1 liter of alcohol was added 72.7 g of triethylamine, and the resulting mixture was then refluxed for 5 hours. After distilling off the alcohol, the residual oily product was dissolved in 1.5 liters of ethyl acetate, and the ethyl acetate layer separated was washed several times with 2 liters of a 5% hydrochloric solution, followed by washing with a 5% aqueous sodium bicarbonate solution. Thereafter, the ethyl acetate layer was dehydrated on sodium sulfate and then concentrated. The residual oily product was recrystallized from benzene to obtain the title compound. The yield was 42.7 g and the melting point was 107°–109° C.

In the manner above illustrated, various couplers may be synthesized in accordance with the aforementioned synthesis processes. Of the couplers obtained in the manner mentioned above, the exemplified compounds were subjected to elementary analysis to obtain the results as shown below.

| Exemplified compound | | Elementary Analytical Value Calculated (%) | Found (%) |
|---|---|---|---|
| (1) | C | 77.06 | 77.32 |
| | H | 10.91 | 10.88 |
| | N | 5.62 | 5.73 |
| (2) | C | 77.92 | 77.68 |
| | H | 11.26 | 11.09 |
| | N | 5.05 | 5.15 |
| (3) | C | 80.15 | 80.05 |
| | H | 11.49 | 11.50 |
| | N | 3.90 | 3.96 |
| (4) | C | 79.71 | 79.66 |
| | H | 11.99 | 11.82 |
| | N | 3.87 | 3.92 |
| (5) | C | 81.69 | 81.91 |
| | H | 10.15 | 9.99 |
| | N | 3.81 | 3.68 |
| (6) | C | 75.91 | 76.76 |
| | H | 8.07 | 8.23 |
| | N | 5.90 | 5.70 |
| (7) | C | 74.03 | 73.97 |
| | H | 10.69 | 10.68 |
| | N | 3.45 | 3.56 |
| (8) | C | 72.37 | 72.37 |
| | H | 10.41 | 10.61 |
| | N | 8.04 | 7.98 |
| (9) | C | 72.37 | 72.50 |
| | H | 10.41 | 10.70 |
| | N | 8.04 | 8.24 |
| (10) | C | 69.12 | 68.92 |
| | H | 7.62 | 7.55 |
| | N | 6.91 | 6.68 |
| | Cl | 5.83 | 5.81 |
| (11) | C | 76.05 | 76.13 |
| | H | 9.33 | 9.48 |
| | N | 6.82 | 6.55 |
| (12) | C | 76.94 | 77.01 |
| | H | 8.74 | 8.83 |
| | N | 5.28 | 5.08 |
| (13) | C | 72.78 | 72.92 |
| | H | 10.69 | 10.98 |
| | N | 3.54 | 3.31 |
| | Cl | 8.95 | 9.20 |
| (14) | C | 65.27 | 64.99 |
| | H | 9.81 | 9.96 |
| | N | 3.17 | 3.21 |
| | S | 7.26 | 7.48 |
| (15) | C | 80.83 | 80.85 |
| | H | 12.44 | 12.58 |
| | N | 3.14 | 3.26 |
| (16) | C | 79.93 | 80.05 |
| | H | 12.08 | 11.94 |
| | N | 3.73 | 3.99 |
| (17) | C | 71.60 | 71.70 |
| | H | 9.92 | 10.01 |
| | N | 4.18 | 4.25 |
| (18) | C | 66.09 | 66.31 |
| | H | 8.97 | 9.03 |
| | N | 6.80 | 7.01 |
| | S | 5.19 | 5.28 |
| (19) | C | 66.65 | 66.58 |
| | H | 6.99 | 7.02 |
| | F | 14.64 | 14.43 |
| | N | 4.32 | 4.36 |
| (20) | C | 70.11 | 70.36 |
| | H | 10.08 | 9.98 |
| | N | 3.41 | 3.25 |
| | Cl | 8.62 | 8.88 |
| (21) | C | 76.31 | 76.63 |
| | H | 11.50 | 11.21 |
| | N | 3.71 | 3.75 |
| (22) | C | 74.93 | 74.68 |
| | H | 10.71 | 11.01 |
| | N | 4.37 | 4.29 |
| (23) | C | 71.20 | 71.53 |
| | H | 10.30 | 10.51 |
| | N | 3.32 | 3.08 |
| (24) | C | 71.90 | 72.18 |
| | H | 8.85 | 8.67 |
| | N | 8.99 | 9.11 |
| (25) | C | 70.07 | 69.79 |
| | H | 10.04 | 9.94 |
| | N | 6.06 | 6.43 |
| (26) | C | 66.63 | 66.90 |
| | H | 8.40 | 8.41 |
| | N | 6.48 | 6.53 |
| | S | 7.40 | 7.11 |
| (27) | C | 73.78 | 73.50 |
| | H | 10.86 | 11.21 |
| | N | 7.17 | 7.30 |
| (28) | C | 76.90 | 76.58 |
| | H | 11.70 | 11.49 |
| | N | 3.45 | 3.60 |
| (29) | C | 69.94 | 70.02 |
| | H | 10.29 | 10.34 |
| | N | 3.40 | 3.11 |
| | Cl | 8.60 | 8.35 |
| (30) | C | 63.91 | 63.79 |
| | H | 8.96 | 9.11 |
| | N | 3.11 | 3.02 |
| | Cl | 23.58 | 23.47 |
| (31) | C | 53.53 | 53.80 |
| | H | 7.98 | 8.19 |
| | N | 2.84 | 2.77 |
| | S | 12.97 | 12.73 |
| (32) | C | 76.70 | 76.67 |
| | H | 10.10 | 9.98 |
| | N | 2.98 | 2.71 |
| | S | 6.81 | 7.12 |
| (33) | C | 76.70 | 76.82 |
| | H | 10.10 | 9.99 |
| | N | 2.98 | 2.99 |
| | S | 6.81 | 6.64 |
| (34) | C | 73.01 | 73.09 |
| | H | 6.72 | 6.44 |
| | N | 4.06 | 3.88 |
| | S | 9.26 | 9.21 |
| (35) | C | 65.56 | 65.51 |
| | H | 7.96 | 7.92 |
| | N | 5.67 | 5.80 |
| | Cl | 14.34 | 14.21 |
| (36) | C | 70.20 | 69.89 |
| | H | 8.04 | 8.09 |
| | N | 11.37 | 11.31 |
| | S | 5.20 | 5.52 |
| (37) | C | 73.21 | 73.50 |
| | H | 11.03 | 10.88 |
| | N | 3.56 | 3.80 |
| | S | 8.13 | 8.37 |
| (38) | C | 69.73 | 69.68 |
| | H | 9.19 | 8.89 |
| | N | 2.71 | 2.94 |
| | Se | 15.28 | — |
| (39) | C | 76.96 | 77.01 |
| | H | 11.70 | 11.77 |
| | N | 3.45 | 3.51 |
| (40) | C | 70.98 | 71.40 |
| | H | 10.56 | 10.38 |
| | N | 3.18 | 3.16 |
| | Cl | 8.06 | 7.89 |
| (41) | C | 68.12 | 67.95 |
| | H | 10.07 | 10.00 |
| | N | 5.48 | 5.17 |
| | Cl | 6.93 | 7.22 |
| (42) | C | 73.04 | 72.81 |
| | H | 11.01 | 10.85 |
| | N | 5.88 | 5.94 |
| (43) | C | 64.01 | 63.95 |
| | H | 8.89 | 8.91 |
| | N | 3.25 | 3.40 |
| | Cl | 16.43 | 16.42 |
| (44) | C | 69.48 | 69.41 |
| | H | 9.99 | 10.20 |
| | N | 2.61 | 2.94 |
| (45) | C | 72.81 | 73.14 |
| | H | 7.92 | 8.06 |
| | N | 5.00 | 5.17 |

-continued

| Exemplified compound | Elementary Analytical Value | | |
|---|---|---|---|
| | | Calculated (%) | Found (%) |
| (46) | C | 77.28 | 77.56 |
| | H | 9.85 | 9.75 |
| | N | 2.91 | 2.77 |
| (47) | C | 70.27 | 70.49 |
| | H | 8.67 | 8.81 |
| | N | 5.46 | 5.74 |
| (48) | C | 57.64 | 57.92 |
| | H | 6.21 | 6.42 |
| | N | 4.20 | 4.01 |
| | F | 19.95 | 20.36 |
| (49) | C | 79.40 | 79.26 |
| | H | 10.45 | 10.32 |
| | N | 3.09 | 3.41 |
| (50) | C | 69.65 | 69.59 |
| | H | 9.09 | 9.13 |
| | N | 2.71 | 2.75 |
| | S | 6.20 | 6.26 |
| (51) | C | 65.29 | 65.27 |
| | H | 8.33 | 8.35 |
| | N | 2.53 | 2.59 |
| | Cl | 6.42 | 6.36 |
| | S | 5.81 | 5.80 |
| (52) | C | 72.92 | 72.60 |
| | H | 9.34 | 9.51 |
| | N | 6.54 | 6.19 |
| (53) | C | 75.28 | 75.35 |
| | H | 8.84 | 8.51 |
| | N | 5.85 | 5.98 |
| (54) | C | 72.80 | 73.05 |
| | H | 8.66 | 8.60 |
| | N | 2.36 | 2.24 |
| | S | 5.40 | 5.28 |
| (55) | C | 69.73 | 69.58 |
| | H | 9.36 | 9.70 |
| | N | 5.42 | 5.36 |
| | S | 6.20 | 6.22 |
| (56) | C | 66.04 | 66.29 |
| | H | 10.20 | 10.25 |
| | N | 6.16 | 6.47 |
| | S | 7.04 | 7.08 |
| (57) | C | 65.37 | 65.33 |
| | H | 8.60 | 8.89 |
| | N | 5.08 | 5.01 |
| | S | 5.82 | 5.91 |
| | Cl | 6.42 | 6.19 |
| (58) | C | 61.84 | 61.87 |
| | H | 8.04 | 8.31 |
| | N | 7.21 | 7.10 |
| | F | 14.67 | 14.50 |
| (59) | C | 75.81 | 75.98 |
| | H | 11.57 | 11.19 |
| | N | 8.04 | 8.04 |
| (60) | C | 79.59 | 79.81 |
| | H | 10.69 | 10.59 |
| | N | 6.19 | 6.08 |
| (61) | C | 76.54 | 76.63 |
| | H | 11.78 | 11.94 |
| | N | 7.44 | 7.48 |
| (62) | C | 71.81 | 71.76 |
| | H | 9.44 | 9.54 |
| | N | 2.79 | 2.87 |
| | S | 6.39 | 6.50 |
| (63) | C | 61.77 | 61.96 |
| | H | 8.53 | 8.69 |
| | N | 4.65 | 4.27 |
| | S | 5.32 | 5.40 |
| (64) | C | 69.80 | 69.80 |
| | H | 10.12 | 10.07 |
| | N | 7.40 | 7.44 |
| (65) | C | 55.85 | 55.97 |
| | H | 7.95 | 7.72 |
| | N | 5.66 | 5.60 |
| | S | 6.48 | 6.70 |
| (66) | C | 56.13 | 56.62 |
| | H | 6.98 | 6.81 |
| | N | 2.42 | 2.37 |
| | S | 11.10 | 11.01 |
| (67) | C | 62.85 | 63.27 |
| | H | 7.35 | 7.18 |
| | N | 5.23 | 5.18 |
| | Cl | 6.63 | 6.54 |
| (68) | C | 63.13 | 63.40 |
| | H | 8.03 | 8.09 |
| | N | 7.12 | 7.45 |
| | S | 5.44 | 5.20 |
| (69) | C | 55.06 | 55.37 |
| | H | 6.41 | 6.37 |
| | N | 6.21 | 6.28 |
| | S | 4.74 | 4.69 |
| | Cl | 5.24 | 4.93 |
| (70) | C | 68.54 | 68.36 |
| | H | 9.78 | 9.49 |
| | N | 7.99 | 8.31 |
| (71) | C | 67.64 | 67.29 |
| | H | 8.51 | 8.56 |
| | N | 3.03 | 3.05 |
| | S | 6.94 | 7.30 |
| (72) | C | 72.97 | 72.88 |
| | H | 9.57 | 9.63 |
| | N | 5.32 | 5.60 |
| (73) | C | 72.37 | 72.61 |
| | H | 10.41 | 10.49 |
| | N | 8.04 | 8.08 |
| (74) | C | 76.81 | 77.07 |
| | H | 8.43 | 8.43 |
| | N | 6.89 | 6.67 |
| (75) | C | 77.78 | 77.90 |
| | H | 12.12 | 12.34 |
| | N | 2.16 | 2.12 |
| | Cl | 5.47 | 5.24 |
| (76) | C | 59.66 | 59.72 |
| | H | 7.33 | 7.01 |
| | N | 7.45 | 7.59 |
| | S | 5.69 | 5.34 |
| (77) | C | 68.54 | 68.73 |
| | H | 8.19 | 8.01 |
| | N | 9.22 | 9.26 |
| (78) | C | 66.48 | 66.28 |
| | H | 8.14 | 8.25 |
| | N | 3.23 | 3.30 |
| | S | 7.39 | 7.51 |
| (79) | C | 66.63 | 66.52 |
| | H | 8.39 | 8.12 |
| | N | 6.47 | 6.37 |
| | S | 7.42 | 7.25 |
| (80) | C | 58.35 | 58.17 |
| | H | 7.44 | 7.62 |
| | N | 2.52 | 2.70 |
| | S | 11.54 | 11.38 |
| (81) | C | 64.68 | 64.96 |
| | H | 8.88 | 8.57 |
| | N | 6.86 | 6.64 |
| (82) | C | 66.03 | 66.20 |
| | H | 9.23 | 9.31 |
| | N | 6.42 | 6.47 |
| (83) | C | 58.35 | 58.23 |
| | H | 7.44 | 7.38 |
| | N | 2.52 | 2.48 |
| | S | 11.54 | 11.44 |
| (84) | C | 67.17 | 67.15 |
| | H | 8.05 | 7.97 |
| | N | 5.60 | 5.38 |
| (85) | C | 57.60 | 57.43 |
| | H | 7.34 | 7.16 |
| | N | 4.63 | 4.68 |
| | F | 25.14 | 24.96 |
| (86) | C | 73.97 | 74.12 |
| | H | 9.31 | 9.40 |
| | N | 6.16 | 6.08 |
| (87) | C | 58.11 | 57.99 |
| | H | 8.58 | 8.58 |
| | N | 5.42 | 5.55 |
| | S | 6.21 | 6.38 |
| (88) | C | 60.51 | 60.42 |
| | H | 8.89 | 8.93 |
| | N | 7.56 | 7.58 |

-continued

| Exemplified compound | Elementary Analytical Value | Calculated (%) | Found (%) |
|---|---|---|---|
| (89) | S | 5.77 | 5.69 |
|  | C | 73.82 | 73.90 |
|  | H | 6.71 | 6.67 |
|  | N | 7.18 | 6.98 |
| (90) | C | 59.58 | 59.44 |
|  | H | 7.31 | 7.40 |
|  | N | 8.02 | 7.89 |
|  | S | 6.12 | 6.06 |
|  | Cl | 6.77 | 6.80 |
| (91) | C | 73.68 | 73.53 |
|  | H | 10.24 | 10.11 |
|  | N | 5.93 | 6.01 |
| (92) | C | 77.31 | 77.28 |
|  | H | 9.47 | 9.60 |
|  | N | 4.87 | 4.91 |
| (93) | C | 67.97 | 68.03 |
|  | H | 9.02 | 9.13 |
|  | N | 2.56 | 2.63 |
|  | S | 5.85 | 5.70 |
| (94) | C | 74.81 | 74.92 |
|  | H | 9.52 | 9.63 |
|  | N | 2.81 | 2.89 |
| (95) | C | 76.78 | 76.75 |
|  | H | 9.55 | 9.61 |
|  | N | 3.09 | 2.99 |
| (96) | C | 69.14 | 69.30 |
|  | H | 9.00 | 8.98 |
|  | N | 2.78 | 2.83 |
|  | S | 6.37 | 6.50 |
| (97) | C | 72.28 | 72.19 |
|  | H | 10.75 | 10.68 |
|  | N | 3.83 | 3.90 |
| (98) | C | 72.92 | 73.03 |
|  | H | 8.26 | 8.32 |
|  | N | 4.25 | 4.33 |
| (99) | C | 73.20 | 73.10 |
|  | H | 8.98 | 9.02 |
|  | N | 6.57 | 6.70 |
| (100) | C | 78.54 | 78.38 |
|  | H | 9.89 | 9.78 |
|  | N | 3.52 | 3.44 |
| (101) | C | 68.53 | 68.33 |
|  | H | 7.35 | 7.38 |
|  | N | 5.00 | 5.01 |
|  | S | 5.72 | 5.83 |
| (102) | C | 65.11 | 65.30 |
|  | H | 9.02 | 9.13 |
|  | N | 9.61 | 9.70 |
|  | Cl | 7.59 | 7.40 |
| (103) | C | 73.20 | 73.10 |
|  | H | 8.98 | 9.10 |
|  | N | 6.57 | 6.55 |
| (104) | C | 67.79 | 67.92 |
|  | H | 8.75 | 8.73 |
|  | N | 6.08 | 5.96 |
|  | S | 6.96 | 7.02 |
| (105) | C | 67.79 | 67.84 |
|  | H | 8.75 | 8.80 |
|  | N | 6.08 | 6.15 |
|  | S | 6.96 | 7.02 |
| (106) | C | 67.57 | 67.30 |
|  | H | 7.09 | 7.03 |
|  | N | 6.56 | 6.60 |
|  | S | 7.52 | 7.38 |
| (107) | C | 80.49 | 80.52 |
|  | H | 9.23 | 9.01 |
|  | N | 3.13 | 3.20 |
| (108) | C | 73.04 | 72.98 |
|  | H | 7.74 | 7.80 |
|  | N | 8.97 | 9.11 |
| (109) | C | 71.49 | 71.63 |
|  | H | 8.67 | 8.73 |
|  | N | 9.26 | 9.10 |
| (110) | C | 62.46 | 62.46 |
|  | H | 9.44 | 9.63 |
|  | N | 7.29 | 7.19 |
|  | S | 8.43 | 8.28 |
| (111) | C | 59.83 | 59.99 |
|  | H | 8.90 | 8.96 |
|  | N | 9.52 | 9.73 |
|  | S | 7.26 | 7.11 |
| (112) | C | 70.78 | 70.59 |
|  | H | 7.33 | 7.44 |
|  | N | 6.97 | 6.89 |
|  | Cl | 5.50 | 5.71 |
| (113) | C | 75.59 | 75.63 |
|  | H | 8.46 | 8.66 |
|  | N | 5.88 | 5.93 |
| (114) | C | 73.03 | 72.87 |
|  | H | 9.29 | 9.31 |
|  | N | 8.24 | 8.36 |
|  | S | 6.29 | 6.18 |
| (115) | C | 68.92 | 68.97 |
|  | H | 8.43 | 8.64 |
|  | N | 6.89 | 7.01 |
|  | S | 10.51 | 10.61 |
| (116) | C | 64.53 | 64.38 |
|  | H | 6.37 | 6.40 |
|  | N | 8.85 | 8.87 |
|  | S | 10.13 | 9.95 |
| (117) | C | 64.33 | 64.50 |
|  | H | 7.60 | 7.63 |
|  | N | 8.34 | 8.21 |
|  | Cl | 7.03 | 7.13 |
| (118) | C | 70.39 | 70.43 |
|  | H | 8.03 | 8.12 |
|  | N | 6.57 | 6.48 |
| (119) | C | 56.04 | 56.18 |
|  | H | 8.47 | 8.45 |
|  | N | 2.61 | 2.65 |
|  | S | 11.97 | 12.11 |
| (120) | C | 64.83 | 64.97 |
|  | H | 8.16 | 8.22 |
|  | N | 6.40 | 5.58 |
|  | S | 6.18 | 6.02 |
| (121) | C | 62.45 | 62.54 |
|  | H | 8.02 | 7.89 |
|  | N | 6.43 | 6.41 |
|  | S | 4.90 | 4.93 |
| (122) | C | 77.38 | 77.52 |
|  | H | 8.81 | 8.85 |
|  | N | 6.45 | 6.32 |
| (123) | C | 78.49 | 78.26 |
|  | H | 10.61 | 10.39 |
|  | N | 5.09 | 5.20 |
| (124) | C | 67.31 | 67.28 |
|  | H | 7.27 | 8.34 |
|  | N | 8.41 | 8.28 |
| (125) | C | 59.76 | 59.84 |
|  | H | 7.52 | 7.71 |
|  | N | 9.96 | 10.01 |
|  | S | 5.70 | 5.63 |
| (126) | C | 66.43 | 66.40 |
|  | H | 7.01 | 6.92 |
|  | N | 8.86 | 8.99 |

The m-aminophenol type coupler of the present invention may be incorporated into a silver halide emulsion according to procedure commonly employed heretofore in the art of so-called internal type of Koda-color type color photography. For example, the present coupler is dissolved in a high boiling organic solvent having a boiling point of 175° C. or higher, such as tricresyl phosphate or dibutyl phthalate, or in a low boiling organic solvent, such as ethyl acetate or butyl propionate, which solvents may be used either singly or in the form of a solvent mixture thereof. Thereafter, the resulting solution is mixed with an aqueous gelatin solution, the mixture is emulsified by dispersion by means of a high speed rotary mixer or colloid mill, and the emulsified dispersion is then incorporated into the silver halide emulsion, or alternatively said emulsified dispersion is divided, after setting, into small portions from which the low boiling organic solvent is removed by such means as water-washing and the like, and the emulsified dispersion thus treated may be incorporated into the silver halide emulsion. Of the present couplers, those which are alkaline-soluble may also be incorporated into the silver halide emulsion by means of a so-called Fisher's dispersion method. Thus, the light-sensitive silver halide photographic material of the present invention contains theren in the m-aminophenol type coupler either in its emulsion layer or the layer or layers adjacent thereto, and the material may also contain at the same time 2 or more kinds of the m-aminophenol type couplers, and if necessary common yellow, magenta and cyan couplers simultaneously therewith.

When a light-sensitive silver halide photographic material thus prepared according to the present invention is developed by use of a common primary aromatic amine type color developing agent, the exposed silver particles on the material are reduced by means of the color developing agent to form a silver image and, on the other hand, the oxidized color developing agent couplers with the m-aminophenol type coupler to give a substantially black dye of indoaniline type. Thus, the light-sensitive silver halide photographic material containing the m-aminophenol type coupler of the present invention is to give a substantially black dye image when subjected to such treatment as color development fixing water-washing, which treatment is the most general treatment system in the current color photography, and any of currently used primary aromatic amine type color developing agents may be used for developing the light-sensitive silver halide photographic materials of the present invention. As particularly preferable color developing agents used in the present invention, there may be mentioned p-aminophenol type and p-phenylenediamine type developing agents, for example, p-aminophenol, N,N-diethyl-p-phenylenediamine, N-ethyl-N-ω-sulfobutyl-p-phenylenediamine, 2-amino-5-diethylaminotoluene, p-amino-N-ethyl-N-β-hydroxyethylaniline, 4-amino-3-methyl-N-ethyl-N-(β-hydroxyethyl)aniline, 4-amino-3-methyl-N-ethyl-N-(β-methoxyethyl)aniline, 4-amino-3-methyl-N-ethyl-N-(β-methysulfonamidoethyl)aniline and p-aminophenols.

In the present invention, further, there may also be used such so-called Dey-Dev compounds, for example, 2,2'-methylenebis(p-aminophenol), N,N'-ethylenebis(4-amino-3-methyl-N-ethylaniline) and the like.

Hydrophilic colloids advantageously usable in the preparation of a light-sensitive emulsion in the light-sensitive silver halide photographic materials of the present invention, include gelatin, gelatin derivatives, colloidal albumin, agar, gum arabic, cellulose, acrylamide, imidopolyacrylamide, casein, polyvinyl alcohol, polyvinyl pyrrolidone, hydrolyzed polyvinyl acetate, polymers obtained by polymerization of protein or saturation acylated protein with a monomer havng a vinyl group, and the like. Usable as silver halide in the light-sensitive silver halide photographic materials used in the present invention, may be any of those which are commonly used in silver halide photographic emulsion, such as silver bromide, silver chloride, silver iodobromide, silver chlorobromide and silver chloroiodobromide.

The silver halide emulsion used in the light-sensitive silver halide photographic materials of the present invention may be prepared according to the commonly practiced method and other various processes, for example, such as disclosed in Japanese Patent Publication No. 7772/1971 or U.S. Pat. No. 2,592,250, that is, the emulsion may be prepared by any process such as for preparing a so-called conversion emulsion or so-called Lippmann's emulsion. The silver halide emulsion thus prepared may be sensitized with chemical sensitizers, for example, such sulfur sensitizers as allylthiocarbamide, thiourea, allylisothiocyanate and cystine, active or inert selenium sensitizers, and noble metal sensitizers including such gold compounds as potassium chloro aurate, auric trichloride, potassium auricthiocyanate, 2-aurothiabenzothiazole methylchloride and the like, such palladium compounds as ammonium chloropalladate and the like, ruthenium compounds, rhodium compounds iridium compounds, which sensitizers may be used either singly or in the form of a suitable combination thereof. The emulsion may be subjected to reduction sensitization using a reducing agent, in addition to the chemical sensitization, and may further be stabilized with triazoles, imidazoles, azaindenes, benzothiazolium compounds, mercaptanes or mixtures thereof, and the emulsion may contain therein sensitizing compounds of thioether type, quaternary ammonium salt type or polyalkylene oxide type. Furthermore, the aforementioned silver halide emulsion may be incorporated with such wetting agents, plasticizers and film property-improving agents, for example, as glycerine, dihydroxyalkanes such as 1,5-pentadiol, esters of ethylenebisglycolic acid, bisethoxydiethyleneglycol succinate and water-dispersible particulate high molecular compounds obtained by emulsion polymerization, and also with various photographic additives, for example, such film hardeners as ethyleneimine type compounds, dioxane derivatives, dicarboxylic acid chlorides and diesters of methanesulfonic acid, such coating aids as saponin and sulfosuccinates, fluorescent whitening agents, antistatic agents and anti-staining agents.

The silver halide photographic emulsion of the present invention is sensitized in the desired light-sensitive spectrum region and hence may also be subjected to optical sensitization by means of suitable sensitizing dyes. Various sensitizing dyes may be usable for this purpose, and they may be used singly or in the form of a combination of two or more kinds.

The light-sensitive silver halide photographic material of the present invention may contain therein, if necessary, various photographic additives, in addition to the compounds previously mentioned. For instance, into a light-sensitive emulsion layer of the layer or layers adjacent thereto, there may be incorporated, for example, such compound as capable of releasing a development inhibitor at the time of development in response to a density of an image being developed, for example such development inhibitor-releasing compounds as disclosed in the Japanese Patent Publication No. 22514/1971 or, for example, tetrazolium compounds, according to the purposes.

The light-sensitive silver halide photographic material of the present invention is prepared by coating the present silver halide photographic emulsion thus incorporated with various photographic additives on a support which has been subjected to corona discharge treatment, fire flame treatment or ultraviolet irradiation treatment, or on a support through a subbing layer or intermediate layer.

Advantageously usable as supports in the present invention, are those which include, for example, baryta paper, polyethylene-coated paper, glass plate, cellulose acetate, cellulose nitrate, polystryene terephthalate and, in addition, polyamide, polycarbonate and polystyrene films.

Preferably, the light-sensitive silver halide photographic material of the present invention is advantageously color developed according to a common color development method employed for developing a so-called internal type light-sensitive silver halide color photographic material, but a so-called incorporated type or Koda-color type color treatment process may also be applicable thereto.

As the internal type color developers usable in the present invention, there may be mentioned, as a typical example, a developer having the under-mentioned composition.

| Composition of developer: | |
| --- | --- |
| Sodium carbonate monohydrate | 10 g |
| Sodium sulfite | 2 g |
| Potassium bromide | 1 g |
| 4-Amino-N,N-diethylaniline sulfate | 6 g |
| Water to make | 1 liter |
| | Adjusted pH to 11.0. |

According to purposes, these developers may contain therein one or more kinds of black-and-white developing agents, for example, Metol, Phenidone and hydroquinone.

After color development treatment using such developer as mentioned above, the developed light-sensitive silver halide photographic material of the present invention may be subjected to common photographic treatment, for example, a combination of treatments suitably selected, using a stopping solution containing an organic acid, a stop-fixing solution containing an organic acid and hypo or such fixing component as ammonium thiosulfate, a fixing solution containing such fixing component as hypo or ammonium thiosulfate, and other processing solutions as a stabilizing solution and the like, and other treatments such as water-washing and drying.

The light-sensitive silver halide photographic material of the present invention may be applicable advantageously to every black-and-white light-sensitive material including negative material for common black-and-white photography, paper for common black-and-white photography, material for X-ray photography, material for photo-lithography or material for common microfilm, and particularly may be effectively applicable to such high silver content black-and-white light-sensitive materials as those for X-ray photography and photolithography, wherein not only the silver content can be greatly reduced but also the speed thereof can be increased.

Further, the light-sensitive material of the present invention may advantageously applicable to such image reinforcing treatment methods, for example, as disclosed in Japanese Patent Publication No. 46419/1974, Japanese Patent Applications Nos. 70907/1974, 80321/1974 and 109213/1974, and a further drastic curtailment of silver content comes to be possible by application of such method to the present invention.

The present invention is illustrated below with reference to examples in more detail, but embodiments of the invention are not limited only thereto.

EXAMPLE 1

10 Grams of compound (9) was added to a mixture of 10 ml of dibutyl phthalate and 30 ml of ethyl acetate and allowed to completely dissolve at 40° C. in the mixture. The solution was mixed with 5 ml of a 10% aqueous solution of Alkanol B (a trade name of a product of alkylnaphthalene sulfonate produced and sold by Du Pont Co.) and 200 ml of a 5% aqueous gelatin solution, and the mixture was emulsified by dispersion by use of a colloid mill, thereby to obtain a coupler dispersion. The coupler dispersion was incorporated into 500 g of a silver iodobromide emulsion (containing 5 mol% of silver iodide) for common black-and-white negative and the emulsion was coated on a cellulose triacetate base so that the amount of silver present in the resulting coating became about 20 mg per 100 $cm^2$ of the coated base (sample A). For comparison, on the other hand, the same emulsion as in the sample A but not containing a dispersion of compound (9) was coated on a cellulose triacetate based so that the amount of silver present in the resulting coating became about 40 mg per 100 $cm^2$ of the coated base (sample B as a control).

After exposure through an optical wedge in the usual way, the samples A and B were individually developed at 20° C. for 6 minutes with a developer having the following composition.

| Metol | 25 g |
| --- | --- |
| Anhydrous sodium sulfite | 30 g |
| Hydroquinone | 25 g |
| Sodium carbonate monohydrate | 10 g |
| Potassium bromide | 0.5 g |
| Water to make | 1 liter |

The samples A and B thus developed were individually subjected in the usual procedure to stopping, fixing and water-washing, thereby to obtain samples A-1 and B-1, respectively. On the other hand, the sample A was exposed to light and then color developed at 20° C. for 6 minutes with a developer having the following composition.

| 4-Amino-3-methyl-N-ethyl-N-methanesulfonamidoethylaniline 3/2 $H_2SO_4$ | 5 g |
| --- | --- |
| Anhydrous sodium sulfite | 25 g |
| Sodium carbonate monohydrate | 20 g |
| 1-Phenyl-3-pyrazolidone | 0.5 g |
| Water to make | 1 liter |

After the development, sample A was subjected in the usual procedure to stopping, fixing and water-washing, thereby to obtain sample A-2.

Sample A-2 was found to give a tone of bluish black color. Samples A-1, A-2 and B-1 were individually subjected to sensitometry, thereby to obtain the results as shown in Table 1.

Table 1

| Sample | Photographic characteristics Notes Specific speed | Gamma | Fog | Dmax |
| --- | --- | --- | --- | --- |
| A-1 | 65 | 0.22 | 0.03 | 1.1 |
| A-2 (Present invention) | 105 | 0.46 | 0.06 | 2.6 |
| B-1 | 100 | 0.43 | 0.05 | 2.7 |

As is clear from Table 1, it was observed that sample A-2 according to the present invention, even though the silver content thereof is only half that of control sample B-1, had a maximum density (Dmax) at substantially the same level as that of the control sample B-1. The specific speed was represented by a relative speed as measured by assuming as 100 the speed of the sample B-1.

The same procedures as above were repeated but using each of compounds (2), (4), (11) and (12) instead of compound (9). The same results were observed equally.

EXAMPLE 2

To a low speed silver chlorobromide emulsion for contact film for photo-lithography was added 500 g of the coupler dispersion as prepared in Example 1, and the emulsion was coated on a cellulose triacetate base so that the amount of silver present in the resulting coating became about 20 mg/100 cm$^2$ (sample A). For comparison, the same emulsion as used in the sample A but not containing the coupler dispersion was coated on a cellulose triacetate base so that the amount of silver present in the resulting coating became about 50 mg/100 cm$^2$ (sample B). Thus, sample B had a silver content substantially identical with those of currently used products of light-sensitive graphic materials, whereas the sample A was a low silver content light-sensitive material, the silver content of which was only 2/5 of that of the sample B.

Samples A and B were individually brought into contact with a screen negative and exposed to light by means of a printer. Thereafter, the samples thus exposed were individually developed at 20° C. for 2 minutes and 30 seconds with a developer having the following composition.

| Metol | 1.5 g |
|---|---|
| Anhydrous sodium sulfite | 23 g |
| Hydroquinone | 6 g |
| Sodium carbonate monohydrate | 41 g |
| Potassium bromide | 1.0 g |
| Water to make | 1 liter |

Samples A and B thus developed were individually fixed and water-washed in the usual procedure to obtain samples A-1 and B-1, respectively. On the other hand, sample A which had been likewise exposed to light was subjected to color development at 20° C. for 2-minutes and 30 seconds with a developer having the following composition.

| 4-Amino-N,N-diethylaniline ½ H$_2$SO$_4$ | 8 g |
|---|---|
| Sodium carbonate monohydrate | 40 g |
| 1-Phenyl-3-pyrazolidone | 0.3 g |
| Anhydrous sodium sulfite | 20 g |
| Potassium bromide | 1.5 g |
| Water to make | 1 liter |

Sample A thus developed was fixed and water-washed in the usual procedure to obtain sample A-2. It was found as a result of a comparative examination that sample A-1, when compared with control sample B-1, was low in dot density and the quality of dot, per se, of sample A-1 was poor. In the case of sample A-2 which had been prepared by subjecting the aforesaid sample A to color development in the manner above illustrated, however, because of the increased bluish black color due to color reaction, sample A-2 was substantially equal in density of as well as in quality of the dot to the control sample B-1, though the silver content of sample A-2 was only 2/5 of that of control sample B-1.

EXAMPLE 3

10 Grams of compound (4) was added to a mixture of 10 ml of tricresyl phosphate and 30 ml of ethyl acetate and allowed to completely dissolve at 50° C. in the mixture. The solution was mixed with 5 ml of a 10% aqueous solution of Alkanol B and 200 ml of a 5% aqueous gelatin solution, and the mixture was emulsified by dispersion by use of a colloid mill to obtain a coupler dispersion. The coupler dispersion was incorporated into 500 g of a silver iodobromide emulsion (containing 5 mol% of silver iodide) for X-ray, and the emulsion was coated on one side of a polyester base so that the amount of silver present in the resulting coating became about 40 mg/100 cm$^2$ (sample A). On the other hand, the same emulsion as in the sample A but not containing said coupler was coated on one side of a polyester base so that the amount of silver present in the resulting coating became 40 mg/100 cm$^2$, thereby to obtain control sample B.

After exposure through an optical wedge, sample B was developed at 20° C. for 5 minutes with a developer having the following composition, followed by usual fixing and water-washing.

| Anhydrous sodium sulfite | 60 g |
|---|---|
| 1-Phenyl-3-pyrazolidone | 0.3 g |
| Hydroquinone | 15 g |
| Anhydrous sodium carbonate | 25 g |
| Potassium bromide | 4 g |
| Benztriazole | 0.3 g |
| Sodium hydroxide | 25 g |
| Water to make | 1 liter |

On the other hand, sample A which had likewise been exposed to light was color developed at 20° C. for 5 minutes with a developer having the following composition, followed by usual fixing and water-washing.

| 4-Amino-N,N-diethylaniline ½ H$_2$SO$_4$ | 8 g |
|---|---|
| Anhydrous sodium sulfite | 25 g |
| Potassium bromide | 3 g |
| 1-Phenyl-3-pyrazolidone | 0.3 g |
| Hydroquinone | 3 g |
| Anhydrous sodium carbonate | 5.0 g |
| Water to make | 1 liter |

It was found as a result of the above treatment that sample A formed thereon a bluish black dye image and a silver image, and had photographic characteristics, when compared with control sample B, as shown in Table 2. In Table 2, the specific speed was represented by a relative value as measured by assuming as 100 the speed of sample B.

Table 2

| Sample | Photographic characteristics Specific speed | Gamma | Fog | Dmax |
|---|---|---|---|---|
| A (present invention) | 115 | 2.6 | 0.05 | 2.3 |
| B (control) | 100 | 1.2 | 0.03 | 1.1 |

As is clear from Table 2, it is understood that the light-sensitive silver halide photographic material according to the present invention has excellent performance as a light-sensitive material for X-ray.

EXAMPLE 4

The same samples as in Example 3 were treated in the same manner as in Example 3 using p-aminophenol as a color developing agent.

It was found as a result of the treatment that sample A produced thereon a slightly brownish black dye image and a silver image, and had a maximum density, when compared with control sample B, as shown in Table 3.

Table 3

| Sample | Dmax |
| --- | --- |
| A | 2.2 |
| B | 1.2 |

EXAMPLE 5

Into a silver chlorobromide emulsion for common black-and-white photographic printing paper was incorporated a dispersion of compound (11). The emulsion was coated on a cellulose triacetate base in the manner as shown in Table 4, and the base was provided on the coated surface with a protective layer consisting of gelatin, a film hardener and an extender.

Table 4

| Sample | Amount of silver (mg/100 cm$^2$) | Amount of coupler (mg/100 cm$^2$) |
| --- | --- | --- |
| A (control) | 13 mg | 0 mg |
| B | 6 mg | 10 mg |
| C | 1.5 mg | 10 mg |

After exposure through an optical wedge, samples A, B and C were individually developed at 20° C. for 1 minute with a developer having the following composition.

| | |
| --- | --- |
| Metol | 1 g |
| Anhydrous sodium sulfite | 7.5 g |
| Hydroquinone | 4 g |
| Sodium carbonate monohydrate | 26.7 g |
| Potassium bromide | 0.7 g |
| Water to make | 1 liter |

Samples A, B and C thus developed were individually subjected to in the usual way to stopping, fixing and water-washing, thereby to prepare samples Nos. 1, 2 and 3. On the other hand, samples B and C which had been separately prepared were individually exposed to light through an optical wedge and the color developed at 20° C. for 1 minute with a developer having the following composition.

| | |
| --- | --- |
| 4-Amino-N,N-diethylaniline ½ H$_2$SO$_4$ | 4 g |
| Anhydrous sodium sulfite | 4 g |
| Sodium carbonate monohydrate | 25 g |
| Potassium bromide | 1.0 g |
| Water to make | 1 liter |

Subsequently, the thus developed samples B and C were individually subjected in the usual manner to stopping, fixing and water-washing, thereby to prepare samples Nos. 4 and 5, respectively.

Furthermore, sample C which had been separately exposed to light through an optical wedge was developed at 20° C. for 1 minute with a developer prepared by adding 2.0 g/l of cobalt III hexamine chloride, followed likewise by stopping, fixing and water-washing, thereby to prepare sample No. 6.

Each of the samples thus prepared was subjected to measurement of a maximum density thereof, thereby to obtain the results as shown in Table 5.

Table 5

| Sample No. | Relative speed | Dmax |
| --- | --- | --- |
| 1 (control) | 100 | 1.4 |
| 2 | 62 | 0.6 |
| 3 | — | — |
| 4 | 168 | 1.4 |
| 5 | — | — |
| 6 | 102 | 1.5 |

Thus, in the case of sample No. 4 where the present compound was used, it is understood that sample No. 4, the silver content of which is only about half that of the control sample, was sufficiently usable even when subjected to the usual development treatment, and that a further drastic curtailment in the silver content could be possible in the case of sample No. 6 which was subjected to the color development effected in the presence of the cobalt hexamine chloride.

EXAMPLE 6

Samples were individually prepared by coating a polyester base on the surface with a coating material such as shown in the following Table 6.

Table 6

| Sample | Amount of silver (mg/100 cm$^2$) | Amount of coupler (mg/100 cm$^2$) |
| --- | --- | --- |
| A | 40 mg | — |
| B | 5 mg | — |
| C | 40 mg | 10 mg |
| D | 5 mg | 10 mg |

On the coated surface of each sample, however, was formed a gelatin protective film containing a film hardener, an extender, etc. As the silver halide emulsion, there was used a silver iodobromide emulsion for X-ray, and in the case of each of samples C and D, compound (7) was protect dispersed together with tricresyl phosphate in the silver iodobromide emulsion in the same manner as in Example 1.

After exposure through an optical wedge, sample A was developed at 20° C. for 5 minutes with the same monochromatic developer as used in Example 3, followed by common fixing and water-washing, thereby to prepare sample No. 1 (control). Also sample B was likewise treated to prepare sample No. 2. Samples C and D were individually color developed at 20° C. for 5 minutes with the same developer as used in Example 3, followed likewise by fixing and water-washing, thereby to prepare samples Nos. 3 and 4, respectively. The developed samples C and D were individually treated further at 20° C. for 5 minutes with a developer having the following composition:

| | |
| --- | --- |
| 4-Amino-N,N-diethylaniline ½ H$_2$SO$_4$ | 7 g |
| Anhydrous sodium sulfite | 20 g |
| Anhydrous sodium carbonate | 50 g |
| Hydroquinone | 5 g |
| 1-Phenyl-3-pyrazolidone | 0.5 g |
| N-Methylbenzthiazolium p-toluene sulfonate | 1.0 g |
| 1-Phenyl-5-mercaptotetrazole | 20 mg |

-continued

| | |
|---|---|
| Water to make | 1 liter |

Subsequently, the thus treated samples C and D were individually subjected to common fixing and water-washing, thereby to prepare samples Nos. 5 and 6, respectively. Of the two samples thus treated, sample D was further treated, after development, at 20° C. for 6 minutes in a hydrogen peroxide bath having the following composition, followed likewise by fixing the water-washing, thereby to prepare sample No. 7.

| | |
|---|---|
| 35% $H_2O_2$ | 25 ml |
| Water to make | 1 liter |

Adjusted to pH 8 by addition of 1 N-NaOH.

Each of the samples thus treated was subjected to measurement of fog and maximum density thereof, thereby to obtain the results as summarized in Table 7.

Table 7

| | Coating conditions | | Treatment conditions | | | | |
|---|---|---|---|---|---|---|---|
| Sample No. | Amount of silver (mg) | Coupler (mg) | Monochromatic development | Color development | $H_2O_2$ treatment | Results | |
| | | | | | | Fog | Dmax |
| 1 (control) | 40 | — | Done | — | — | 0.04 | 1.1 |
| 2 | 5 | — | Done | — | — | — | — |
| 3 | 40 | 10 | — | Done | — | 0.04 | 2.2 |
| 4 | 5 | 10 | — | Done | — | — | — |
| 5 | 40 | 10 | — | Done | — | 0.05 | 2.6 |
| 6 | 5 | 10 | — | Done | — | — | — |
| 7 | 5 | 10 | — | Done | Done | 0.07 | 2.9 |

Reviewing the results as shown in Table 7, it is understood that by using the present compound in combination with the hydrogen peroxide reinforcement treatment, a further drastic curtailment in the silver content of the light-sensitive silver halide photographic material.

EXAMPLE 7

Using a low speed silver chlorobromide emulsion for graphic purposes and an alkali dispersion of compound (17), samples as shown in Table 8 were individually prepared.

Table 8

| Sample | Amount of coating Silver (mg/100 cm²) | Coupler (mg/100 cm²) |
|---|---|---|
| A (control) | 40 | — |
| B | 20 | 8 |
| C | 4 | 8 |

Separately, subjected to supersonic wave dispersion was a mixture of 15 ml of a 5% aqueous solution of DES (sodium di-(ethylhexyl succinate)-sulfonate), 60 ml of a 10% aqueous gelatin solution, 200 mg of 1,3,5-triphenyl-tetrazolium chloride (hereinafter abbreviated to "T-salt") and 35 ml of water. The liquid thus dispersed was incorporated into a mixture of the aforesaid emulsion and coupler dispersion, and the resulting mixture was coated according to the manner as shown in Table 9 on a cellulose triacetate film base to prepare samples shown in said table.

Table 9

| Sample | Amount of coating Silver (mg/100 cm²) | Coupler (mg/100 cm²) | 1,3,5-triphenyl tetrazolium chloride (mg/100 cm²) |
|---|---|---|---|
| D | 40 | — | 2 |
| E | 20 | 8 | 2 |
| F | 4 | 8 | 2 |

Samples A, B, C, D, E and F were individually exposed in the usual way to light through a crossline screen and treated in the following manner. Samples A and D were individually developed at 20° C. for 2 minutes and 30 seconds with a developer having the following composition, followed by common fixing and water-washing, thereby to prepare samples Nos. 1 and 4, respectively.

| | |
|---|---|
| Metol | 1.5 g |
| Anhydrous sodium sulfite | 20 g |
| Hydroquinone | 6 g |
| Sodium carbonate monohydrate | 40 g |
| Potassium bromide | 1.0 g |
| Water to make | 1 liter |

Samples B and E were individually developed at 20° C. for 2 minutes and 30 seconds with a developer having the following composition, followed by fixing and water-washing, thereby to prepare samples Nos. 2 and 5, respectively.

| | |
|---|---|
| 4-Amino-N,N-diethylaniline ½ $H_2SO_4$ | 7 g |
| 1-Phenyl-3-pyrazolidone | 0.5 g |
| Anhydrous sodium sulfite | 20 g |
| Sodium carbonate monohydrate | 40 g |
| Potassium bromide | 1.0 g |
| Water to make | 1 liter |

Samples C and F were individually developed in the same manner as in the case of the samples Nos. 2 and 5 with the above-mentioned developer. Thereafter, the developed samples C and F were individually treated at 20° C. for 5 minutes with a hydrogen peroxide amplification bath having the following composition, followed by fixing and water-washing, thereby to prepare samples Nos. 3 and 6, respectively.

| | |
|---|---|
| 35% H₂O₂ | 25 ml |
| Water to make | 1 liter |

Adjusted pH with 1 N NaOH to 8.
The results obtained were as summarized in Table 10.

Table 10

| Sample No. | Coating conditions | | | Treatment conditions | | | Results | |
|---|---|---|---|---|---|---|---|---|
| | Silver | Coupler | T-salt | Monochromatic development | Color development | $H_2O_2$ treatment | Dmax | Dot |
| 1 | 40 mg | — | — | Done | — | — | 2.0 | Bad |
| 2 | 20 mg | 8 mg | — | — | Done | — | 2.1 | Bad |
| 3 | 4 mg | 8 mg | — | — | Done | Done | 2.6 | Bad |
| 4 | 40 mg | — | 2 mg | Done | — | — | 2.0 | Good |
| 5 | 20 mg | 8 mg | 2 mg | — | Done | — | 2.0 | Good |
| 6 | 4 mg | 8 mg | 2 mg | — | Done | Done | 2.5 | Good |

Reviewed the results, it is understood that the samples containing T-salt gave excellent dots of good image quality even when treated with a common developer which was not a special developer for light-sensitive photolithographic material, and that when the T-salt was used in combination with the present coupler in a light-sensitive silver halide graphic material, a sufficient density and dot of good image quality could be obtained thereby even when the silver content of said material was only about half that commonly used in the materials of this kind and, in addition, similar results could be obtained by use of a light-sensitive silver halide graphic material containing the T-salt and the present coupler but having a drastically curtailed silver content when the material was treated with a hydrogen peroxide reinforcement bath.

EXAMPLE 8

Compound (18) was alkali dispersed in the usual manner. The alklai dispersion was then incorporated into a silver iodobromide emulsion (containing 5 mol% of silver iodide) for X-ray, and the emulsion was coated in the manner as shown in Table 11 on one side of a polyester base, thereby to prepare samples.

Separately, the same emulsion as above but not containing the present coupler was likewise coated on a polyester base, thereby to prepare a sample used as a control.

Table 11

| Sample | Amount added Silver (mg/100 cm²) | Coupler (mg/100 cm²) |
|---|---|---|
| A (control) | 40 | — |
| B | 40 | 13 |
| C | 7 | 13 |

Sample A was developed at 20° C. for 5 minutes with a monochromatic developer having the same composition as in the developer used in Example 3, followed by fixing and water-washing, thereby to prepare sample No. 1 (control).

Sample B was color developed at 20° C. for 5 minutes with the same color developer containing the 4-amino-N,N-diethylaniline as in Example 3, followed by fixing and water-washing, thereby to prepare sample No. 2.

After color development as in the case of sample B, sample C was treated at 20° C. for 5 minutes with a hydrogen peroxide reinforcement bath having the same composition as in the base used in Example 7, thereby to prepare sample No. 3.

The results obtained were as summarized in Table 12.

Table 12

| Photographic characteristics Sample No. | Fog | Dmax |
|---|---|---|
| 1 | 0.03 | 1.2 |
| 2 | 0.04 | 2.3 |
| 3 | 0.05 | 2.5 |

As is clear from Table 12, it is understood that the expected object could be accomplished even by use of the alkali dispersion type coupler according to the present invention and, the amount of silver contained in the present sample could be curtailed to about half the amount commonly required when the sample was intended to be subjected to the common color development and the amount of silver could be drastically curtailed when the present sample was intended to be treated further with the hydrogen peroxide amplification bath.

EXAMPLE 9

A high speed silver iodobromide photographic emulsion was prepared by subjecting, after the first ripening, a silver iodobromide emulsion to chemical sensitization with a sulfur sensitizer, a gold sensitizer and the like, followed by stabilization using tetrazaindenes and other stabilizers.

Separately, compounds (4), (13), (44) and (50) were individually protect-dispersed, according to the same procedure as in Example 3, in a dibutyl phthalate/ethyl acetate mixture to prepare coupler dispersions. Each of the coupler dispersions thus prepared was incorporated into the aforesaid silver iodobromide photographic emulsion and the resulting emulsion was coated on a polyester base. Subsequently, a gelatin protective layer containing a spreading agent and a hardener was formed on the emulsion-coated polyester base. In the manner mentioned above, there were prepared samples of light-sensitive silver halide photographic materials containing their respective ingredients as shown below.

Table 13

| Sample | Amount of compound added (mg/dm²) | Amount of silver added (mg/dm²) | Amount of gelatin used (mg/dm²) | Amount of dibutyl phthalated added (mg/dm²) |
|---|---|---|---|---|
| A | — | 39.2 | 26.2 | — |
| B | (1) 19.0 | 43.2 | 28.1 | 10.1 |
| C | (1) 18.1 | 21.5 | 27.5 | 9.2 |
| D | (8) 19.8 | 19.2 | 25.8 | 10.0 |

Table 13-continued

| Sample | Amount of compound added (mg/dm$^2$) | Amount of silver added (mg/dm$^2$) | Amount of gelatin used (mg/dm$^2$) | Amount of dibutyl phthalated added (mg/dm$^2$) |
|---|---|---|---|---|
| E | (32) 21.8 | 18.1 | 24.7 | 9.8 |
| F | (38) 27.2 | 23.6 | 28.4 | 9.1 |

The samples thus prepared were individually exposed to light through an optical wedge in the usual manner. Sample A was subjected to development with the black-and-white developer described in Example 3 in the similar manner to prepare a sample 1. Samples B, C, D, E and F were individually subjected to color development at 20° C. for 3 minutes with a color developer having the following composition:

| | |
|---|---|
| 4-Amino-N,N-diethylaniline sulfate | 6 g |
| Sodium carbonate monohydrate | 10 g |
| Potassium bromide | 1.0 g |
| Sodium sulfite | 10 g |
| 5-Nitrobenzimidazole | 150 mg |
| Distilled water to make | 1 liter |

Adjusted pH with sodium hydroxide to 11.0

Samples B–F thus color-developed were then subjected to stopping, fixing and water-washing to prepare samples 2–6, respectively. Each of Samples 2–6 had a slightly bluish black image thereon. Samples 1–6 thus developed were individually subjected to sensitometry to obtain the results as shown below.

Table 14

| Sample | Fog | Dmax | Gamma |
|---|---|---|---|
| 1 (control) | 0.05 | 1.3 | 1.1 |
| 2 | 0.06 | 2.8 | 2.6 |
| 3 | 0.04 | 1.4 | 1.3 |
| 4 | 0.07 | 2.9 | 2.7 |
| 5 | 0.05 | 2.2 | 2.1 |
| 6 | 0.06 | 2.4 | 2.3 |

As is clear from the foregoing, it is understood that even the samples containing compound (4) form thereon a very good black image and, on the other hand, in the samples containing such active point-substituted type couplers as compounds (13), (44) and (50) the silver content thereof may be reduced by about one-half, as compared with the sample containing the active point-unsubstituted type coupler, and said silver content may be reduced by about one-fourth, as compared with the control sample containing only silver without any coupler as aforesaid.

EXAMPLE 10

On a polyethylene terephthalate base were successively formed the following layers according to the procedure as described in Example 3.

(1) Layer containing high speed silver iodobromide emulsion for X-ray, which layer contains 19 mg/dm$^2$ of gelatin, 25 mg/dm$^2$ of silver and 16 mg/dm$^2$ of compound (13).

(2) Gelatin protective layer, containing 11 mg/dm$^2$ of gelatin.

The sample thus prepared was exposed to light through an optical wedge and the exposed sample was then developed at 20° C. for 3 minutes with the same color developer as in Example 9. The sample thus developed was then subjected in the usual manner to stopping and fixing, followed by water-washing, whereby a negative film sample having formed thereon a bluish black dye image was obtained. The negative film sample was the subjected to sensitometry to obtain the results showing fog of 0.08 and Dmax of 2.2.

As is clear from the foregoing, it is understood that the silver content of the negative film sample prepared by this example may be reduced by one-third or less, as compared with the prior art films for X-ray.

EXAMPLE 11

A green-sensitive silver iodobromide emulsion for X-ray, into which compound (30) had been incorporated, was coated according to the procedure of Example 3 on a polyethylene terephthalate base to obtain a sample containing:

(1) 23 mg/dm$^2$ of gelatin,
21 mg/dm$^2$ of silver, and
15 mg/dm$^2$ of the exemplified compound (30), and (2) gelatin protective layer containing 10 mg/dm$^2$ of gelatin.

The sample thus obtained was exposed to X-ray at a distance of 1 m, 70 KV peak and 100 MA through an aluminum wedge using a sensitizing paper of GTH Ortho type produced by Tokyo Shibaura Elect. Co., Ltd.

The thus exposed sample was color-developed at 20° C. for 3 minutes with the developer of Example 9, and the developed sample was subjected to fixing and water-washing, followed by drying. The image formed on the developed sample consisted of a black dye image, and the sample was subjected to sensitometry to obtain the results showing fog of 0.05, Dmax of 2.9 and gamma of 2.6.

From the foregoing, it is understood that the present sample, even when used as an ortho type film for X-ray, forms a desired image without deteriorating image quality and the silver content thereof can be reduced to one-fourth of that required in the presently used films for X-ray.

EXAMPLE 12

A light-sensitive element was prepared by coating on a polyethylene terephthalate base a light-sensitive layer containing a chemically sensitized silver iodobromide emulsion containing 19 mg/dm$^2$ of gelatin, 30 mg/dm$^2$ of silver and 18 mg/dm$^2$ of the exemplified compound (65).

Separately, an image-receiving element was prepared by forming the following layers successively in the under-mentioned order.

(1) pH-Reducing layer containing 100 mg/dm$^2$ of poly(methylvinyl ether/maleic anhydride).

(2) Gelatin intermediate layer, containing 3 mg/dm$^2$ of gelatin.

(3) Dye image-receiving layer containing 100 mg/dm$^2$ of copoly(styrene-N-benzyl-N,N-dimethyl-N-(3-maleimidopropyl)ammonium chloride).

The light-sensitive element was exposed to light through an optical wedge. Thereafter, a processing composition as mentioned below was passed so as to spread in a sandwitch form between the exposed light-sensitive element and the image-receiving element placed one upon the other through a pair of rollers facing to each other.

| Composition of the processing composition: | |
| --- | --- |
| Benzyl alcohol | 10.0 ml |
| Sodium hydroxide | 25.0 g |
| 4-Amino-N-ethyl-N-β-hydroxyethyl aniline sulfate | 30.0 g |
| 5-Nitrobenzimidazole | 0.05 g |
| Hydroxyethylcellulose | 30.0 g |
| Piperidinohexosereductone | 0.2 g |
| Distilled water to make | 1 liter |

The light-sensitive and image-receiving elements thus treated were left to stand at about 20° C. for 80 seconds and the two elements were then peeled off from each other. The image-receiving element was then acidified with a 2% aqueous acetic acid solution and washed with water. The image-receiving element had thereon a transferred bluish black dye negative image corresponding to the image-wise exposure. The results of sensitometry shown Dmax of 1.92 and Dmin of 0.24.

EXAMPLE 13

Example 3 was repeated, except that compounds (99) and (108) were individually used in place of compound (4) to obtain the results as shown in the following table:

Table 15

| Photographic characteristics Sample | Specific speed | Gamma | Fog | Dmax |
| --- | --- | --- | --- | --- |
| A (99) | 114 | 2.5 | 0.05 | 2.2 |
| B (108) | 116 | 2.5 | 0.04 | 2.3 |
| C (control) | 100 | 1.2 | 0.02 | 1.0 |

EXAMPLE 14

Following the procedure described in Example 9, there were prepared samples of light-sensitive silver halide photographic materials containing their respective ingredients as shown below Table 16

| Sample No. | Amount of compound added (mg/dm²) | Amount of silver added (mg/dm²) | Amount of used gelatin (mg/dm²) | Amount of dibutyl phthalate added (mg/dm²) |
| --- | --- | --- | --- | --- |
| A | — | 40.1 | 26.5 | — |
| B | (4) 18.9 | 42.7 | 28.2 | 9.5 |
| C | (20) 19.1 | 21.6 | 28.5 | 9.5 |
| D | (42) 18.4 | 20.8 | 27.4 | 9.2 |
| E | (85) 18.5 | 20.9 | 27.5 | 9.3 |

The sample thus prepared were individually processed in the same manner as in Example 9 and the processed samples were measured in fog, D max and gamma to obtain the results as shown below.

Table 17

| Sample | Fog | Dmax | γ |
| --- | --- | --- | --- |
| A | 0.05 | 1.3 | 1.1 |
| B | 0.06 | 2.7 | 2.6 |
| C | 0.04 | 2.4 | 2.3 |
| D | 0.05 | 2.5 | 2.3 |
| E | 0.05 | 2.3 | 2.3 |

From the above table, it is understood that the present compounds form very favorable black images in the same manner as in Example 9, and that in the light of the results obtained in samples C and E, the split off group (referred to in the specification) may be located either at the p-position of the amino group (i.e. the 6-position of 3-aminophenol) or at an ordinary active point of the cyan coupler (i.e. the 4-position of 3-aminophenol).

EXAMPLE 15

In order to demonstrate the incontestable superiority of the compounds of the present invention over those disclosed in U.S. Pat. No. 2,728,660 and D.P. 1,163,144, the following experiment was conducted in the manner mentioned below.

The compounds used in this experiment were as follows:

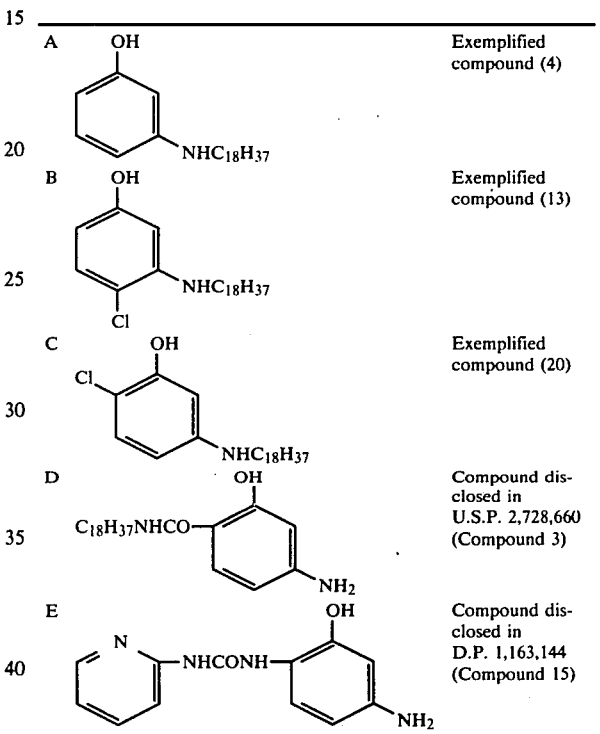

A — Exemplified compound (4)
B — Exemplified compound (13)
C — Exemplified compound (20)
D — Compound disclosed in U.S.P. 2,728,660 (Compound 3)
E — Compound disclosed in D.P. 1,163,144 (Compound 15)

The above-mentioned couplers were individually incorporated into a silver iodobromide emulsion for roentogen photography, and each emulsion was coated on a polyethylene terephthalate base. (The emulsions containing couplers B and C, respectively, were coated so that the coated amount of silver became ½ of that of emulsions containing couplers A, D and E, respectively.). After forming a protective layer on the surface of each sample of the light-sensitive silver halide photographic materials thus prepared, the sample was subjected to color development according to the procedure described in Example 3. Each developed sample was then processed at 20° C. for 8 minutes with a Sakura bleaching solution for negative purpose, and then subjected according to usual procedure to fixing, water-washing and drying.

Photographic properties of each sample as measured were shown below.

Table 18

| Sample No. | Fog | γ | Dmax | B/R | G/R |
| --- | --- | --- | --- | --- | --- |
| A | 0.04 | 2.6 | 2.4 | 1.01 | 0.97 |
| B | 0.05 | 2.7 | 2.7 | 1.03 | 0.89 |
| C | 0.04 | 2.3 | 2.3 | 1.01 | 0.88 |

Table 18-continued

| Sample No. | Fog | γ | Dmax | B/R | G/R |
|---|---|---|---|---|---|
| D | 0.05 | 2.8 | 2.8 | 0.18 | 0.23 |
| E | 0.06 | 2.3 | 2.3 | 0.21 | 0.26 |

In determining the above-mentioned photographic properties, samples A, B and C were individually measured in density by the use of a neutral light and a white light, samples D and E were individually measured in density by the use of a red light (644 mµ).

In the above table, B/R represented a blue density/red density, G/R represented a green density/red density, the blue density was measured at 436 mµ, green density at 546 mµ, and red density at 644 mµ.

From the results shown in the above table, it is understood that differently from compounds such as compounds D and E individually having a group which is not capable of splitting off on the coupling reaction with an oxydation products of a primary amine type color developing agent at the 6-position of 3-aminiphenol, the present compounds are capable of forming very favorable black dye images.

Separately, samples A, B, C, D and E were individually subjected to color development. Each of the developed samples was treated with a 0.05% pronase solution to decompose gelatin and the dye was extracted with n-butanol. The extract was developed with a suitable developing solvent by means of a thin layer chromatography (packed with silica gel; manufactured by Merck) to find that couplers A, B and C (present compounds) formed black dyes, whereas couplers D and E (outside the present invention) merely gave ordinary cyan dyes without forming black dyes.

From the foregoing results, it is understood that such couplers as disclosed, for example, in U.S. Pat. No. 2,728,660 and D.P. 1,163,144, having a group which is not capable of splitting off at the p-position of the amino group do not form black dye images.

What we claim is:

1. A light-sensitive silver halide photographic material comprising an m-aminophenol type coupler represented by the formula,

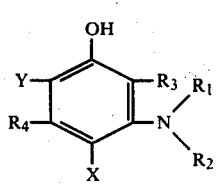

wherein $R_1$ and $R_2$ individually represent a hydrogen atom, an alkyl group, an aryl group, an alkenyl group, or an aralkyl group; $R_3$ and $R_4$ individually represent a hydrogen atom, a halogen atom, a hydroxyl, an alkyl group, an alkoxy group, an alkylamido group, an arylamido group, an alkylsulfonamido group or an arylsulfonamido group; and X and Y individually represent a hydrogen atom, halogen atom or a group capable of being split off on the coupling reaction with an oxidation product of a primary amine type color developing agent, said group selected from the group consisting of sulfo and its salts, carboxyl and its salts, an alkoxy group, an aryloxy group, an alkylcarbonyloxy group, an alkylsulfonyloxy group, an arylcarbonyloxy group, an arylsulfonyloxy group, an alkylcarbamoyloxy group, an arylcarbamoyloxy group, a halogen-substituted alkylamido group, a halogen-substituted arylamido group, an alkylsulfonamido group, an arylsulfonamido grou, 5- or 6-membered imido-group, an arylthio group, an arylseleno group, an arylsulfonyl group, an arylazo group, or a 5- or 6-membered heterocyclic thio group containing in the molecular structure 1 to 4 nitrogen atoms, or one of X and Y is hydroxyl, mercapto, amino, an alkylamino group or an arylamino group, and the other is hydrogen atom, a halogen atom or a split-off group as defined above, said coupler not containing a color developing agent moiety in its molecular structure, whereby said coupler reacts with two molecules of an oxidation product of an aromatic primary amino color developing agent to form a neutral black dye image.

2. A light-sensitive silver halide photographic material according to claim 1 wherein $R_1$, $R_2$ and $R_3$ individually represent a hydrogen atom.

3. A light-sensitive silver halide photographic material according to claim 2 wherein the primary amine type color developing agent is a p-phenylenediamine-type color developing agent.

4. A light-sensitive silver halide photographic material according to claim 1 comprising an m-amino phenol type coupler selected from the group consisting of N-Decyl-m-aminophenol

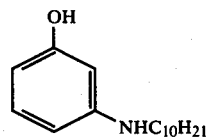

N-Dodecyl-m-aminophenol

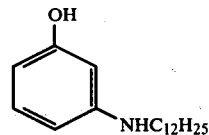

N-Octadecenyl-m-aminophenol

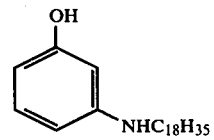

N-Octadecyl-m-aminophenol

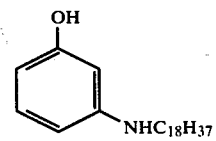

3-(p-Dodecylbenzylamino)phenol

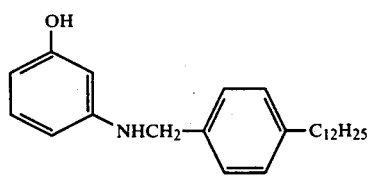

3-[4-(2,4-di-tert-Aminophenoxyacetamido)anilino]-phenol

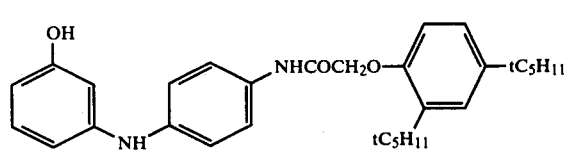

3-{[α-(Hexadecyloxycarbonyl)ethyl]amino}phenol

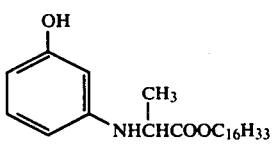

N-[α-(Dodecylcarbamoyl)ethyl]-m-aminophenol

N-[β-(Dodecylcarbamoyl)ethyl]-m-aminophenol

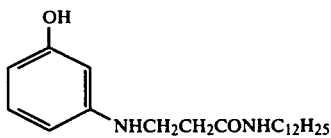

N-{β-[2-Chloro-5-(2,4-di-tert-amylphenoxybutylamido)phenylcarbamoyl]ethyl}-m-aminophenol N-(4-Lauroylamidophenethyl)-m-aminophenol

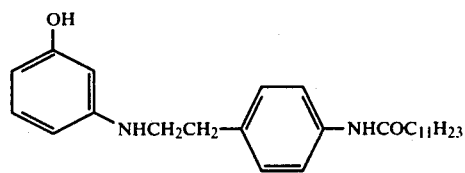

N-{4-[α-(2,4-di-tert-Amylphenoxy)propionamido]-phenethyl}-m-aminophenol

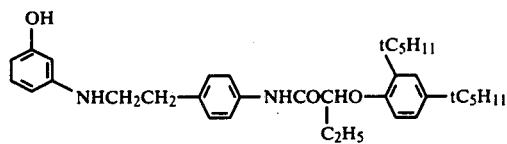

4-Chloro-N-octadecyl-m-aminophenol

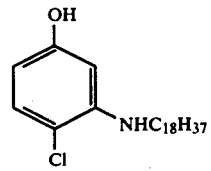

4-Sulfo-N-octadecyl-m-aminophenol

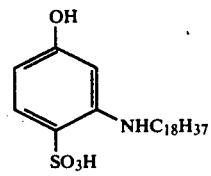

N,N-Didodecyl-m-aminophenol

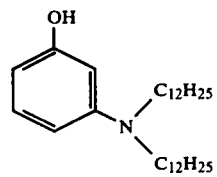

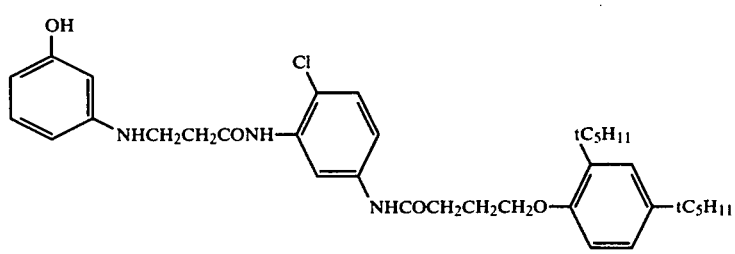

N-Methyl-N-octadecyl-m-aminophenol

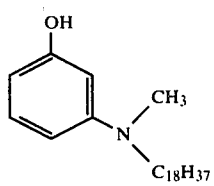

N-{α-Carboxytridecyl}-m-aminophenol

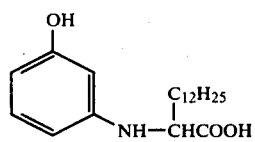

N-{β-[2-sulfo-5-(N-methyl-N-octadecylamino)phenyl-carbamoyl]ethyl}-m-aminophenol

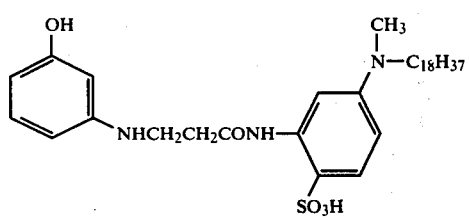

6-Chloro-N-octadecyl-m-aminophenol

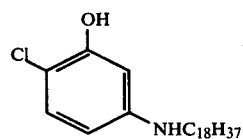

5-Ethoxy-3-hexadecyl-m-aminophenol

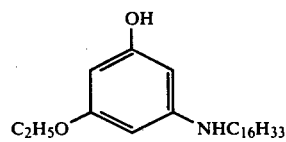

5-Dodecyloxy-m-ethylaminophenol

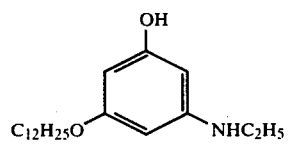

5-Hydroxy-3-{N-[α-(hexadecyloxycarbonylethyl)]amino}phenol

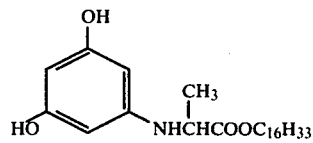

5-Benzoylamido-3-{α-(dodecylcarbamoyl)ethylamino}phenol

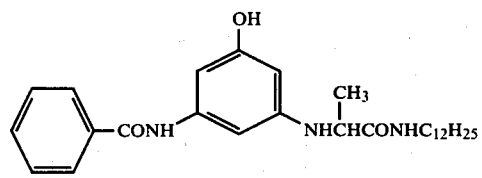

2-Acetamido-3-{α-(hexadecyloxycarbonyl)ethylamino}phenol

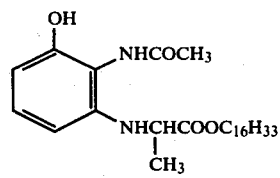

2-Benzensulfonylamido-3-dodecylaminophenol

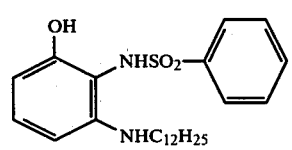

2-Palmiticacidamido-3-N-ethylaminophenol

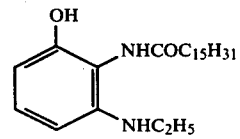

2,5-Dimethyl-3-N-oxtadecylaminophenol

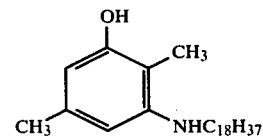

2-Hydroxy-4-chloro-5-N-octadecylaminophenol

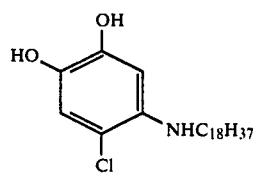

2,4,6-Trichloro-3-N-octadecylaminophenol

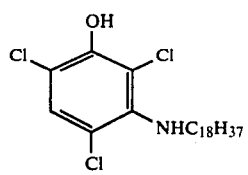

2,4-Disulfo-5-N-hexadecylaminophenol

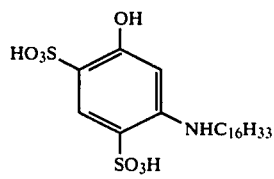

4-Phenylthio-3-N-octadecylaminophenol

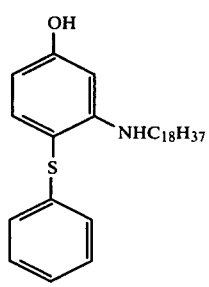

6-Phenylthio-3-N-octadecylaminophenol

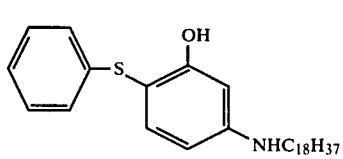

2,4-Diphenylthio-5-{4-(2,4-di-tert-amylphenoxyacetamido)anilino}phenol

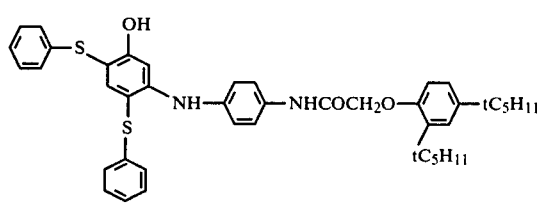

2-Chloro-4-phenylthio-5-[{β-(dodecylcarbamoyl)ethyl}amino]phenol

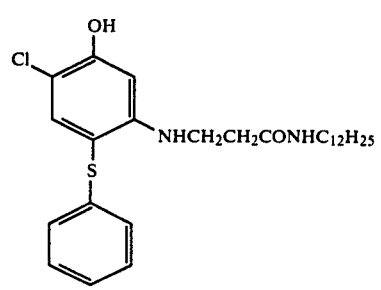

4-(1-Phenyltetrazolium-5-thio)-3-[β-(m-pentadecylphenoxy)ethylamino]phenol

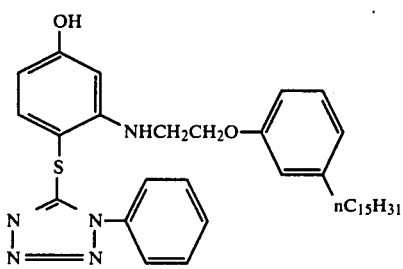

2-Mercapto-5-N-octadecylaminophenol

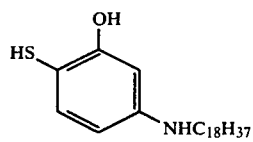

4-Phenylseleno-3-N-octadecylaminophenol

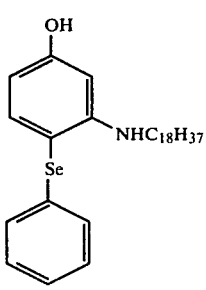

4-Ethoxy-3-N-octadecylaminophenol

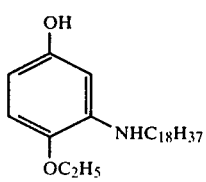

2-Chloroethoxy-5-N-octadecylaminophenol

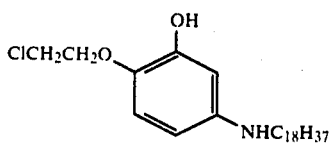

2-Chloro-4-(iso-propylcarbamoylmethoxy)-5-N-octadecylaminophenol

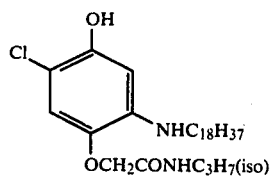

4-(iso-Propylcarbamoylmethoxy)-3-N-octadecylaminophenol

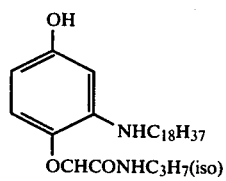

2,4-Dichloro-3-methoxy-5-N-hexadecylaminophenol

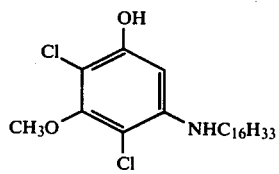

4-Butoxycarbonylmethoxy-3-{[α-(hexadecyloxycarbonyl)ethyl]amino}phenol

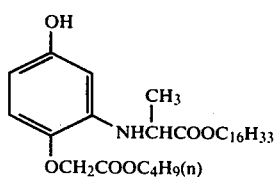

4-(p-Carboxyphenoxy)-3-{[α-(p-dodecylphenylcarbamoyl)ethyl]amino}phenol

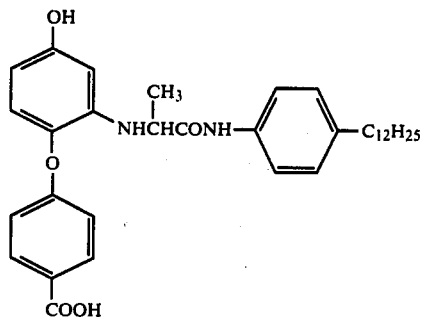

4-Benzoyloxy-3-N-dodecylaminophenol

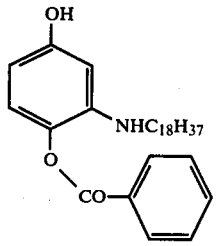

4-Acetoxy-3-[(O-hexadecyloxyphenylcarbamoyl)methylamino]phenol

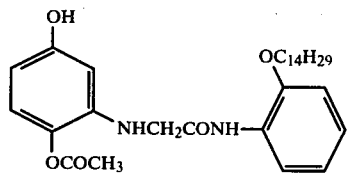

4-Perfluoropropyl-3-[(O-hexadecyloxyphenylcarbamoyl)methylamino]phenol

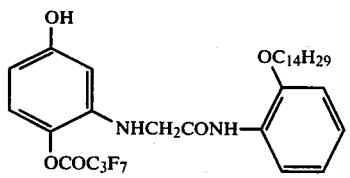

2-Phenoxy-5-N-octadecylaminophenol

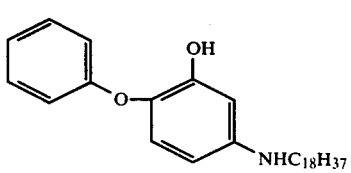

4-Benzensulfonyloxy-3-N-octadecylaminophenol

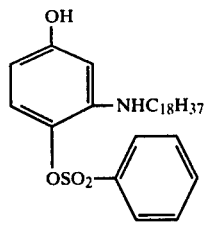

2-Chloro-4-benzensulfonyloxy-5-N-octadecylamino-phenol

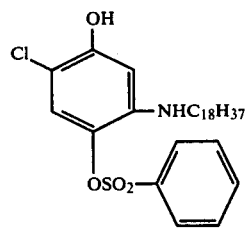

2-Succimido-5-N-hexadecylaminophenol

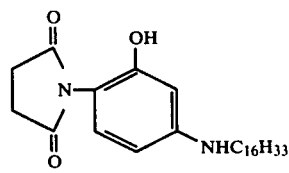

4-Phthalimido-5-N-hexadecylaminophenol

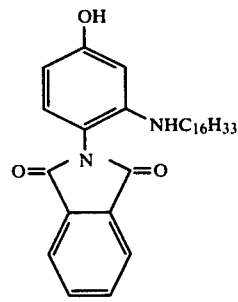

4-(p-Benzensulfonylphenoxy)-3-N-octadecylamino-phenol

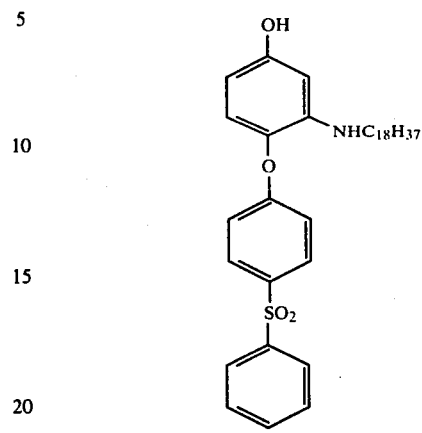

4-Phenylsulfonylamido-3-N-octadecylaminophenol

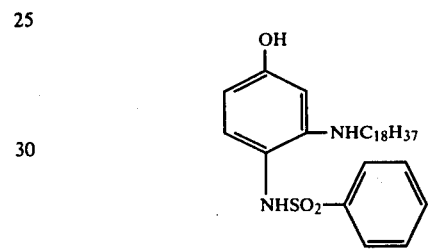

4-Methanesulfonylamido-3-N-octadecylaminophenol

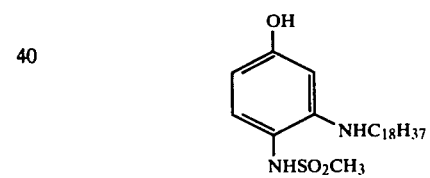

2-Phenylsulfonylamido-4-chloro-3-N-octadecylamino-phenol

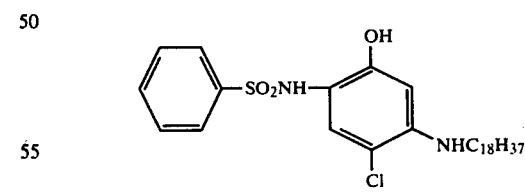

4-Trifluoroacetamido-3-N-dodecylaminophenol

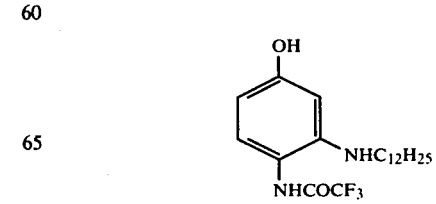

2-Amino-5-N-hexadecylaminophenol

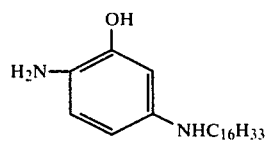

2-Anilino-5-N-octadecylaminophenol

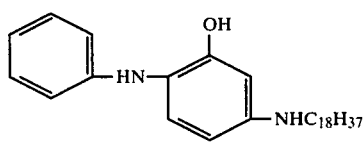

2-Ethylamino-5-N-hexadecylaminophenol

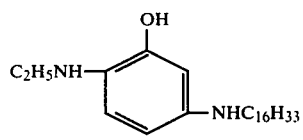

4-Phenylsulfonyl-3-N-octadecylaminophenol

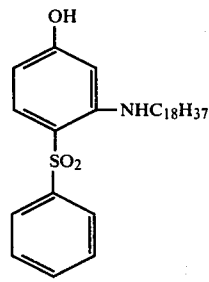

2-Octadecylsuccimido-5-γ-sulfopropylaminophenol sodium salt

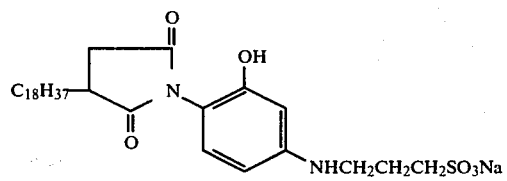

4-Dodecylcarbamoylmethoxy-3-N-ethylaminophenol

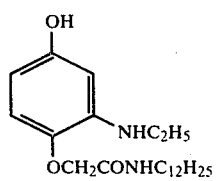

4-Dodecylcarbamoylmethoxy-3-N-(ω-sulfo-propylamino)phenol sodium salt

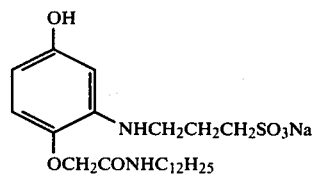

4-(p-Dodecylbenzensulfonyloxy)-3-N-(ω-sulfo-propylamino)phenol sodium salt

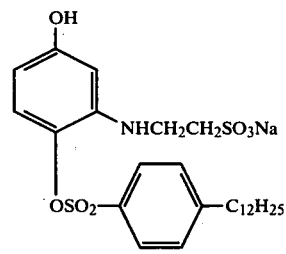

2-Chloro-4-(o-dodecylphenyl)carbamoylmethoxy-5-N-carboxymethylaminophenol

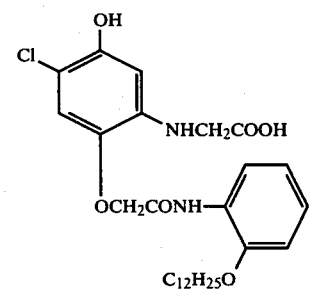

2-(m-Palmiticacidamidophenylsulfonamido)-5-(N-methoxycarbonylmethylamino)phenol

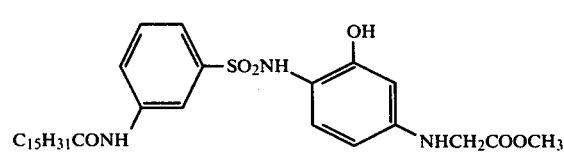

4-[2-Chloro-{5-[d-dodecyloxycarbonyl)ethoxy]carbonyl}phenylazo]-3-(N-γ-sulfopropylamino)phenol

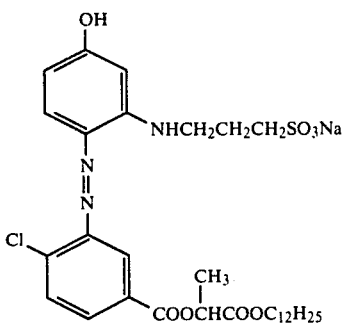

4-Dodecylcarbamoylmethoxy-3-aminophenol

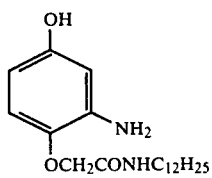

4-(p-Dodecylbenzensulfonyloxy)-3-N-ethylaminophenol

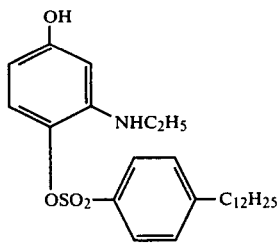

4-p-Methoxyphenylcarbamoyloxy-3-N-octadecylaminophenol

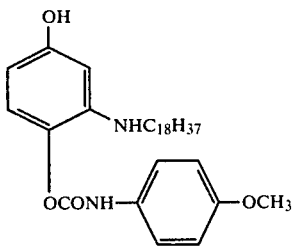

N-[β-(Dodecylcarbamoyl)ethyl]-m-aminophenol

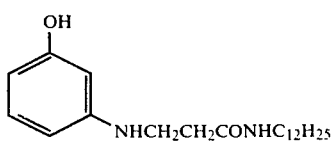

N-(4-Lauroylamidophenethyl)-m-aminophenol

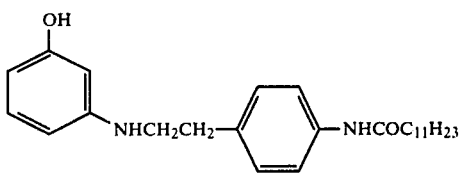

4-Chloro-3-(N,N-di-n-octadecylamino)phenol

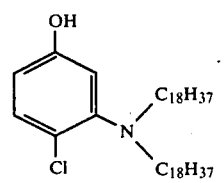

4-{(3-Lauroylamidophenyl)carbamoyloxy}-3-(N-γ-sulfopropyl)aminophenol

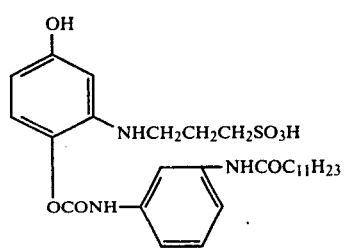

4-{(3-Lauroylamidophenyl)carbamoylmethoxy}-m-aminophenol

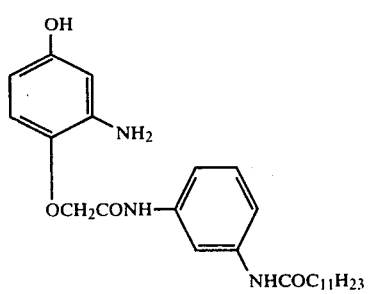

4-(Dodecylbenzensulfonyloxy)-m-aminophenol

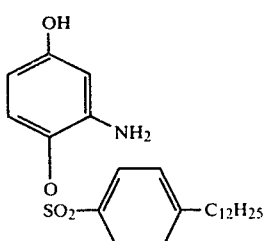

4-(Dodecylbenzensulfonylamino)-m-aminophenol
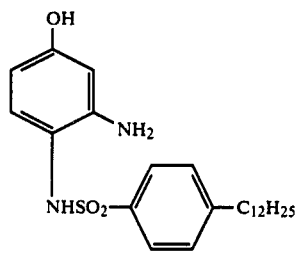
4-(Dodecylcarbamoylmethoxy)-3-(N-carboxymethyl-)aminophenol
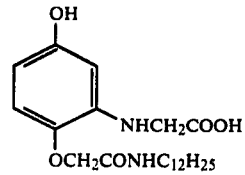
4-(Dodecylcarbamoylmethoxy)-3-(ethyloxycarbonyl-methyl)-aminophenol
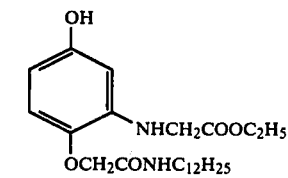
* * * * *